US012625140B2

(12) United States Patent
Zheng et al.

(10) Patent No.: US 12,625,140 B2
(45) Date of Patent: May 12, 2026

(54) MULTIPLEXED IMAGING WITH NANOBODY PROBES

(71) Applicant: Akoya Biosciences, Inc., Menlo Park, CA (US)

(72) Inventors: Yi Zheng, Dover, MA (US); Julia Kennedy-Darling, Redwood City, CA (US); Peter J. Miller, Cambridge, MA (US)

(73) Assignee: Akoya Biosciences, Inc., Menlo Park, CA (US)

( * ) Notice: Subject to any disclaimer, the term of this patent is extended or adjusted under 35 U.S.C. 154(b) by 985 days.

(21) Appl. No.: 17/530,406

(22) Filed: Nov. 18, 2021

(65) Prior Publication Data

US 2022/0155311 A1 May 19, 2022

Related U.S. Application Data

(60) Provisional application No. 63/115,593, filed on Nov. 18, 2020.

(51) Int. Cl.
*G01N 21/64* (2006.01)
*B82Y 5/00* (2011.01)
(Continued)

(52) U.S. Cl.
CPC ............. *G01N 33/582* (2013.01); *G01N 1/30* (2013.01); *G01N 33/54346* (2013.01);
(Continued)

(58) Field of Classification Search
CPC .. G01N 33/582; G01N 1/30; G01N 33/54346; G01N 33/6854;
(Continued)

(56) References Cited

U.S. PATENT DOCUMENTS 7,555,155 B2 6/2009 Levenson et al.
9,909,167 B2 3/2018 Samusik et al.
(Continued)

FOREIGN PATENT DOCUMENTS

WO WO 2005/040769 5/2005
WO WO 2018/022809 2/2018 ............. A61K 51/10
(Continued)

OTHER PUBLICATIONS

Pleiner, Tino, Mark Bates, and Dirk Görlich. "A toolbox of anti-mouse and anti-rabbit IgG secondary nanobodies." Journal of Cell Biology 217.3 (2018): 1143-1154. (Year: 2018).*
(Continued)

*Primary Examiner* — Jennifer Wecker
*Assistant Examiner* — Oyeleye Alexander Alabi
(74) *Attorney, Agent, or Firm* — Wolf, Greenfield & Sacks, P.C.

(57) ABSTRACT

Methods include (a) contacting a biological sample with a composition featuring a plurality of different types of probes, where each type of probe of the plurality of different types of probes includes a detection moiety that selectively binds to a different type of protein target in the sample, a nanobody bound to the detection moiety, and an oligonucleotide linked to the nanobody and featuring an oligonucleotide sequence, where the oligonucleotide sequence of each type of probe is different from the oligonucleotide sequences of each of the other types of probes of the plurality of probes; and (b) contacting the sample with a set of one or more different types of optical labels, where each different type of optical label of the set of optical labels includes an oligonucleotide that selectively hybridizes to only one type of probe.

23 Claims, 12 Drawing Sheets

(51) Int. Cl.

| | | |
|---|---|---|
| *B82Y 30/00* | (2011.01) | |
| *B82Y 40/00* | (2011.01) | |
| *C07F 5/02* | (2006.01) | |
| *C09B 57/00* | (2006.01) | |
| *C09K 11/06* | (2006.01) | |
| *G01N 1/30* | (2006.01) | |
| *G01N 15/10* | (2024.01) | |
| *G01N 15/1429* | (2024.01) | |
| *G01N 27/626* | (2021.01) | |
| *G01N 31/22* | (2006.01) | |
| *G01N 33/483* | (2006.01) | |
| *G01N 33/543* | (2006.01) | |
| *G01N 33/58* | (2006.01) | |
| *G01N 33/68* | (2006.01) | |

(52) U.S. Cl.
CPC ............ *G01N 33/6854* (2013.01); *B82Y 5/00* (2013.01); *B82Y 30/00* (2013.01); *B82Y 40/00* (2013.01)

(58) Field of Classification Search
CPC ... G01N 2021/6421; G01N 2021/6441; G01N 21/6428; B82Y 5/00; B82Y 30/00; B82Y 40/00; C12Q 1/6804
See application file for complete search history.

(56) References Cited

U.S. PATENT DOCUMENTS

| | | | |
|---|---|---|---|
| 10,000,796 B2 | 6/2018 | Samusik et al. | |
| 10,006,082 B2 | 6/2018 | Samusik et al. | |
| 10,126,242 B2 | 11/2018 | Miller et al. | |
| 10,370,698 B2 | 8/2019 | Nolan et al. | |
| 2014/0364329 A1* | 12/2014 | Tao | G01N 33/6845 506/9 |
| 2018/0030504 A1* | 2/2018 | Nolan | G01N 33/5308 |

FOREIGN PATENT DOCUMENTS

| | | | | |
|---|---|---|---|---|
| WO | WO 2018/167141 | 9/2018 | ............ | G01N 33/53 |
| WO | WO 2019/149692 | 8/2019 | ........... | G01N 33/532 |
| WO | WO-2020074905 A1 * | 4/2020 | ......... | C07K 14/4725 |
| WO | WO 2020/163397 | 8/2020 | | |
| WO | WO 2021/067475 | 4/2021 | ........... | C12Q 1/6804 |
| WO | WO 2021/091611 | 5/2021 | ........... | C12Q 1/6804 |

OTHER PUBLICATIONS

The International Search Report and Written Opinion of the International Searching Authority for International Application No. PCT/US2021/059982, dated Mar. 9, 2022.

Fabricius et al., "Rapid and efficient C-terminal labeling of nanobodies for DNA-PAINT", *Journal of Physics D: Applied Physics*, vol. 51, No. 47, pp. 474005 (8pp) (Oct. 19, 2018).

Mu et al., "Influenza virus detection with pentabody-activated nanoparticles", *Journal of Virological Methods*, vol. 169, No. 2, pp. 282-289 (Nov. 1, 2010).

U.S. Appl. No. 63/229,064, filed Aug. 3, 2021, Miller et al.

Arbabi Ghahroudi et al., "Selection and identification of single domain antibody fragments from camel heavy-chain antibodies," Sep. 1997, FEES Lett. 414(3): 521-526.

Bernardinelli at al., "A compact nanobody-DNAzyme conjugate enables antigen detection and signal amplification," May 2020, New Biotechnology 56: 1-8.

English et al., "Ancient species offers contemporary therapeutics: an update on shark VNAR single domain antibody sequences, phage libraries and potential clinical applications," Jan. 2020, Antibody Therapeutics 3(1): 1-9.

Faget et al., "Tyramide Signal Amplification for Immunofluorescent Enhancement," 2015, Methods Mal. Biol. 1318: 161-172.

Gong et al., "Simple Method To Prepare Oligonucleotide-Conjugated Antibodies and Its Application in Multiplex Protein Detection in Single Cells," Jan. 2016, Bioconjugate Chem. 27(1): 217-225.

Harmsen et al., "Properties, production, and applications of camelid single-domain antibody fragments," Nov. 2007, Appl. Microbiology and Biotechnology, 77(1): 13-22.

International Preliminary Report on Patentability in International Appln. No. PCT/US2021/059982, mailed on Jun. 1, 2023, 8 pages.

Pleiner et al., "A toolbox of anti-mouse and anti-rabbit IgG secondary nanobodies," Mar. 2018, J Cell Biol. 217(3): 1143-1154.

Sograte-Idrissi et al., "Nanobody Detection of Standard Fluorescent Proteins Enables Multi-Target DNA-PAINT with High Resolution and Minimal Displacement Errors," Jan. 2019, Cells 8(1): 48.

Wiener et al., "Preparation of single- and double-oligonucleotide antibody conjugates and their application for protein analytics," Jan. 2020, Scientific Reports 10: 1457.

\* cited by examiner

MULTIPLEXED IMAGING WITH NANOBODY PROBES

CROSS-REFERENCE TO RELATED APPLICATIONS

This application claims priority to U.S. Provisional Application No. 63/115,593, filed on Nov. 18, 2020, the entire contents of which are incorporated herein by reference.

TECHNICAL FIELD

This disclosure relates to multiplexed imaging of biological samples, probes for use in multiplexed imaging, and imaging kits.

BACKGROUND

Immuno-labeling can be used to target molecules in samples such as cells, tissue, and other biological specimens. High sensitivity and specificity enables reliable detection of low-abundance targets.

SUMMARY

The disclosure relates to multiplexed analysis of tissue samples. Methods, compositions, and reagent kits for labeling target molecules with oligonucleotide-barcoded detection molecules are described. High-performance barcoded antibodies can be generated using oligonucleotide-conjugated nanobodies that selectively bind to antibodies with high affinity. A biological sample is incubated with a cocktail of detection molecules labeled with oligonucleotides containing barcode sequences. Imaging is performed by introducing a readout moiety conjugated to an oligonucleotide sequence that contains a countersense sequence to one of the barcode sequences.

In an aspect, the disclosure features methods for detecting multiple target compounds in a sample that include contacting a sample with a cocktail containing a plurality of detection moieties, each of which includes a detection molecule and a nanobody conjugated to an oligonucleotide label with a barcode sequence, and subjecting it to an incubation period, subjecting the sample to one or more wash steps, introducing a readout moiety featuring a readout molecule coupled to an oligonucleotide that includes a countersense sequence to a barcode sequence associated with one of the detection moieties, hybridizing the readout moiety with the detection moiety based on the barcode sequence, and imaging the sample.

Embodiments of the methods can include any one or more of the following features.

The nanobody species can bind to targets in the detection molecules with high affinity. The detection molecules can be antibodies. The cocktail can contain multiple antibody species of the same species and isotype. The cocktail can also contain fragments of the nanobody target for one or more nanobody species. The nanobodies can be conjugated using site-specific conjugation. The sample can be subjected to fixation after the wash steps.

The readout moiety can include barcoded fluorescent dyes. The readout moiety can include an enzyme. The readout moiety can include biotin. The sample imaging can include fluorescent imaging.

The methods can include dehybridizing the readout moiety from the detection moiety and repeating at least some of the steps for additional barcode sequences. Multiple species of readout moiety can be introduced at the same time.

Embodiments of the methods can also include any of the other features described herein, including any combinations of features individually described in connection with different embodiments, except as expressly stated otherwise.

In another aspect, the disclosure features reagent kits that include a nanobody moiety conjugated to an oligonucleotide label with a barcode sequence, where the nanobody binds with high affinity to a target in the antibody.

Embodiments of the reagent kits can include any one or more of the following features.

The target can be one of rabbit IgG, mouse IgG1, mouse IgG2a, mouse IgG2b, mouse IgG2c, and mouse IgG3. The kits can include fragments of the target. The kits can include barcoded readout molecules.

Embodiments of the reagent kits can also include any of the other features described herein, including any combinations of features individually described in connection with different embodiments, except as expressly stated otherwise.

In another aspect, the disclosure features methods that include: (a) contacting a biological sample with a composition featuring a plurality of different types of probes, where each type of probe of the plurality of different types of probes includes a detection moiety that selectively binds to a different type of protein target in the sample, a nanobody bound to the detection moiety, and an oligonucleotide linked to the nanobody and featuring an oligonucleotide sequence, where the oligonucleotide sequence of each type of probe of the plurality of probes is different from the oligonucleotide sequences of each of the other types of probes of the plurality of probes; (b) contacting the sample with a set of one or more different types of optical labels, where each different type of optical label of the set of optical labels comprises an oligonucleotide that selectively hybridizes to only one type of probe among the plurality of different types of probes, and an optical moiety; and (c) obtaining at least one image of the sample, where the at least one image includes optical signals generated by at least one of the optical moieties of the set of optical labels.

Embodiments of the methods can include any one or more of the following features.

The methods can include identifying one or more protein targets in the sample based on the optical signals in the at least one image of the sample. The methods can include determining an amount of at least one protein target in the sample based on the optical signals in the at least one image of the sample.

The set of one or more different types of optical labels can include multiple different types of optical labels. The set of one or more different types of optical labels can include at least three different types of optical labels. The detection moiety of at least one of the different types of probes can include an antibody or antibody fragment.

The composition can include at least 10 different types of probes, e.g., at least 30 different types of probes. One or more of the optical moieties of the set of optical labels can include fluorescent dyes. For one or more of the different types of probes among the plurality of different types of probes, the nanobody is bound to the detection moiety with a dissociation constant $K_d$ that is $1.0 \times 10^{-9}$ mol/L or less.

The composition can include multiple different types of probes featuring antibody binding moieties of a common species and isotype. The composition can include at least one type of fragment of a binding target of at least one of the nanobodies among the different types of probes. The composition can include multiple types of fragments of binding targets of multiple nanobodies among the different types of probes.

The methods can include, prior to contacting the sample with the composition, forming each of the different types of probes, where each different type of probe is formed by contacting the binding moiety for the probe with a labeling moiety featuring the nanobody for the probe linked to the oligonucleotide for the probe, and incubating the binding moiety and the labeling moiety to bind the nanobody to the binding moiety. The nanobody can undergo site-specific binding to the binding moiety.

The methods can include, following step (a), contacting the sample with at least one fixative. The methods can include, following step (a), washing the sample to remove unbound probes from the sample.

At least one of the different types of optical labels can include an oligonucleotide linked to an optical moiety through a streptavidin-biotin linkage. The at least one image can include at least one fluorescence image of the sample.

The methods can include repeating steps (b)-(c) with at least one additional set of one or more different types of optical labels, to obtain at least one additional image of the sample that includes optical signals generated by at least one of the optical moieties of the at least one additional set of optical labels. The methods can include identifying one or more additional protein targets in the sample based on the optical signals in the at least one additional image of the sample.

The methods can include, for each sequence of steps (b)-(c), removing the set of one or more different types of optical labels from the sample prior to repeating step (b) with at least one additional set of one or more different types of optical labels. Removing the set of one or more different types of optical labels can include dehybridizing the set of one or more different types of optical labels from the plurality of different types of probes.

Embodiments of the methods can also include any of the other features described herein, including any combinations of features individually described in connection with different embodiments, except as expressly stated otherwise.

In another aspect, the disclosure features reagent kits that include a composition featuring a probe for a target protein analyte in a biological sample, the probe including a detection moiety that selectively binds to the target protein analyte, a nanobody bound to the detection moiety, and an oligonucleotide linked to the nanobody, where a dissociation constant $K_d$ between the nanobody and the detection moiety is $1\times10^{-9}$ mol/L or less.

Embodiments of the kits can include any one or more of the following features.

The detection moiety can include an antibody or antibody fragment. The kits can include a plurality of different types of probes for different target protein analytes in the sample, where each type of probe includes a detection moiety that selectively binds to a different target protein analyte relative to the other probes of the composition, a nanobody bound to the detection moiety, and an oligonucleotide linked to the nanobody and featuring a nucleotide sequence that is different from nucleotide sequences of oligonucleotides of all other types of probes in the composition. The composition can include at least 10 different types of probes.

A target of the nanobody can include one member selected from the group consisting of rabbit IgG, mouse IgG1, mouse IgG2a, mouse IgG2b, mouse IgG2c, and mouse IgG3. The composition can include at least one type of fragment of the target.

The composition can be a first composition, and the kits can include a second composition that includes an optical label featuring an oligonucleotide that selectively hybridizes to the probe and an optical moiety. The optical moiety can include a fluorescent dye.

The composition can be a first composition, and the kits can include a second composition featuring a set of one or more different types of optical labels, where each different type of optical label of the set of optical labels includes an oligonucleotide that selectively hybridizes to only one type of probe among the plurality of different types of probes, and an optical moiety. Each different type of optical label in the set of one or more different types of optical labels can include a different optical moiety. Each of the different optical moieties can include a fluorescent dye.

Embodiments of the kits can also include any of the other features described herein, including any combinations of features individually described in connection with different embodiments, except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying description. Other features and advantages will be apparent from the description and claims.

DESCRIPTION OF DRAWINGS

Like reference symbols in the various drawings indicate like elements.

DETAILED DESCRIPTION

Introduction

Figure 1:
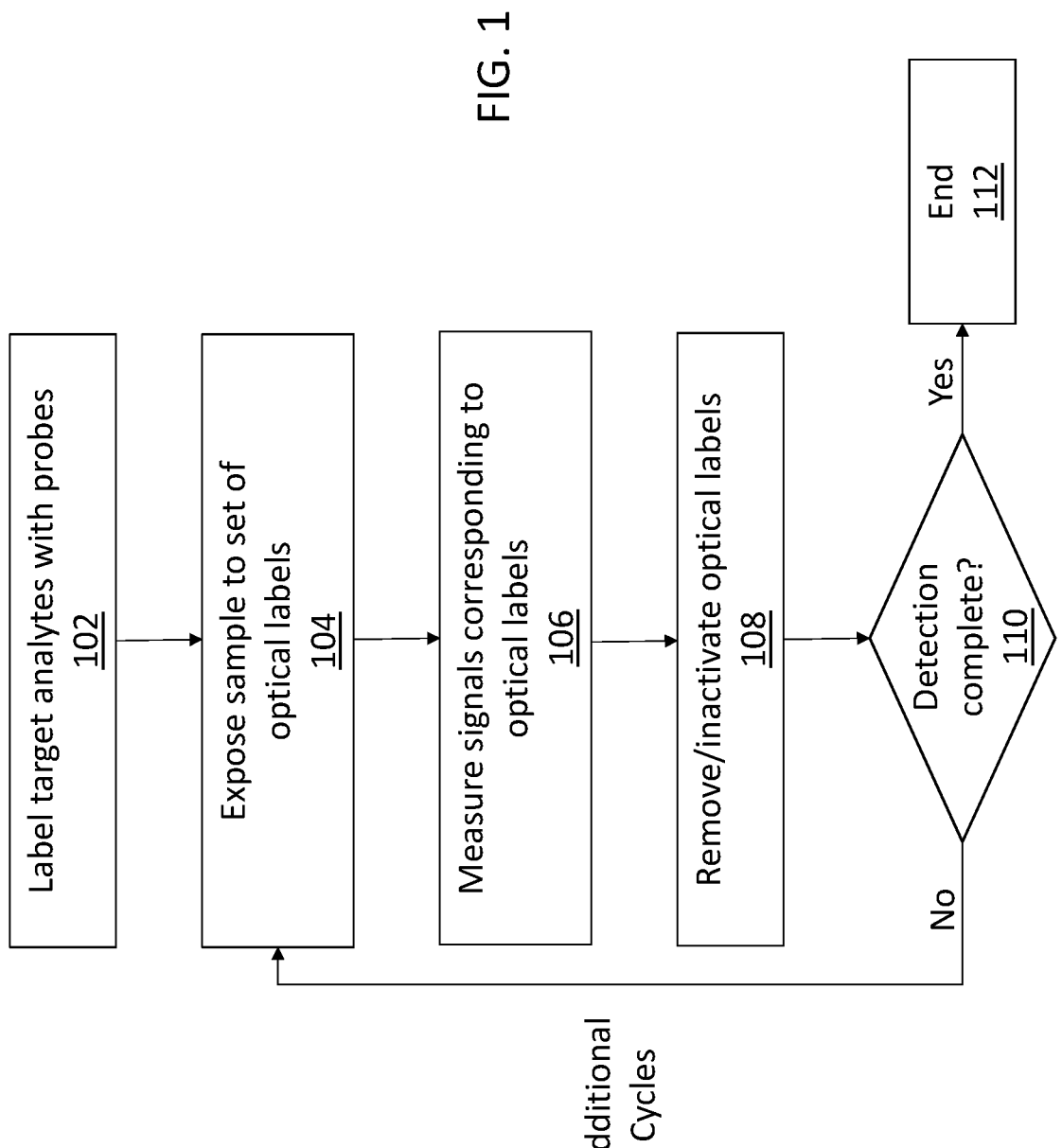
FIG. 1 is a flow chart showing a set of examples steps for detecting target analytes in a biological sample.

Certain multiplexed imaging techniques involve selectively labeling different protein targets in a biological sample with different detection molecules. Provided that the detection molecules are distinguishable and unambiguously label different protein targets, the presence or absence of the different protein targets in the sample can be determine qualitatively and quantitatively.

Commonly in such methods, the detection molecules that are used generate a detectable signal. For example, detection molecules can include different fluorescent species (e.g., fluorescent dyes) that exhibit different fluorescence emission spectra. Samples containing the detection molecules can be spectrally imaged to detect the presence and location of different fluorescent species in the sample, and therefore, the protein targets with which the different fluorescent species are identified.

Some of the most straightforward methods for detecting protein targets in this manner involve introducing into the sample detection molecules that include a primary antibody conjugated to a fluorescent species. Different types of detection molecules include different primary antibodies that are specific to different protein targets, and different fluorescent species, where each type of fluorescent species is conjugated to only one type of primary antibody. By exposing the sample to multiple different detection molecules, the presence of multiple different protein targets in the sample can be determined.

There are practical limitations on the number of different fluorescent species that can be identified from multispectral images that include contributions from each of the species, primarily due to the difficulty of separating the multispectral images into individual contributions from each of the species. Fluorescent species typically have broadband spectra that may be complex, and so computational methods for separating spectrally-overlapping measured signals arising from different fluorescent species are challenging to implement as the number of different fluorescent species increases beyond about 8-10.

Solutions to the problem of spectral congestion in multispectral imaging and detection have been developed. For example, in some methods, detection molecules are introduced into the sample and imaged in groups. That is, the detection methodology involved multiple cycles, and in each cycle, detection molecules are introduced and the sample is imaged. Typically, although not always, detection molecules in the sample are removed or inactivated prior to a subsequent cycle. Such methods can involve a detection molecule such as an antibody that is labeled with an oligonucleotide. Fluorescent species that are conjugated to complementary oligonucleotides are introduced and hybridize to antibody-conjugated oligonucleotides, and the fluorescent species are detected.

CODEX® reagents and methods (available from Akoya Biosciences, Menlo Park, CA) have been developed that involve incubating a sample with a cocktail of many species of such detection molecules, each of which localizes at a different species of target molecule. Multiple target compounds can be detected in a sample by introducing a reporter molecule such as a fluorescent molecule conjugated to a countersense oligonucleotide sequence for a selected label, hybridizing it with its counterpart label, and imaging the sample. The readout moiety may then be de-hybridized and washed away. This process can be repeated many times, enabling visualization and measurement of many targets in the sample. Aspects and reagents involved in such methods are described, for example, in U.S. Pat. Nos. 10,370,698; 10,006,082; 10,000,796; and 9,909,167, the entire contents of each of which are incorporated herein by reference.

Conventional methods for primary antibody labeling (e.g., with fluorescent species or oligonucleotides) have limitations such as yield loss, degradation of functionality due to conjugation at undesirable sites on the antibody, unknown or variable number of labels per primary antibody, requirements for the antibody to be in pure formulation (that is, free of stabilizing proteins), and requirements for verification with gel tests.

Consequently, antibody conjugation is typically performed as an experimental, lot-based task, is costly, involves production cycles where quality and performance can be uncertain, and yields labeled antibody lots with properties vary from lot to lot. For some antibody clones, the labeled antibody does not perform with the sensitivity and/or specificity of the unconjugated antibody, and may even be completely unusable.

The methods described herein can use labeled nanobodies to conjugate labeling species to primary antibodies to form detection molecules that can subsequently be detected in a sample. In general, the degree-of-labeling for each nanobody is predictable and repeatable. Labeled nanobodies can be conjugated to primary antibodies just prior to introduction into a sample to form detection molecules via a simple incubation step, forming detection molecules that bind to specific protein targets via specific interactions between the primary antibodies and corresponding antigens in the sample. Because nanobodies bind to known sites on primary antibodies that are distinct from antigen binding sites, the resulting detection molecules bind predictably to protein targets with comparable specificity and sensitivity to the antibody alone.

As used herein, the term "nanobody" refers to an antibody fragment consisting of a single monomeric variable antibody domain. A "nanobody" is also referred to as a "single-domain antibody" (sdAb). Nanobodies typically have molecular weights of between 12 kDa and 15 kDa, and typically include peptide chains of between 90 and 120 amino acids. $V_HH$ fragment nanobodies can be obtained from heavy-chain antibodies found in camelid species. $V_{NAR}$ fragment nanobodies can be obtained from heavy-chain antibodies derived from cartilaginous fish species. Nanobodies can also be obtained from variable domains of common IgG derived from humans or mice. It should be understood that while most nanobodies are derived from heavy-chain variable domains of antibodies, nanobodies can also be derived from light-chain antibody domains. Methods for nanobody production are described, for example, in Harmsen et al., *Appl. Microbiology and Biotechnology* 77(1): 13-22 (2007), in English et al., *Antibody Therapeutics* 3(1): 1-9 (2020), and in Arbabi Ghahroudi et al., *FEBS Lett.* 414(3): 521-526 (1997), the entire contents of each of which are incorporated by reference herein.

Sample Labeling and Target Detection

FIG. 1 is a schematic diagram of a flow chart showing a set of example steps for detecting protein target analytes in a sample. In a first step 102, the target analytes are labeled with probes. In general, the terms "probe" and "detection molecule" are used interchangeably herein to refer to a molecule that includes a binding moiety that selectively binds to a target analyte in the sample, and a labeling moiety linked to the binding moiety. In the methods described herein, a probe can either be formed prior to introduction into the sample, or can be partially or fully formed in situ within the sample.

Figures 2A, 2B, 2C:
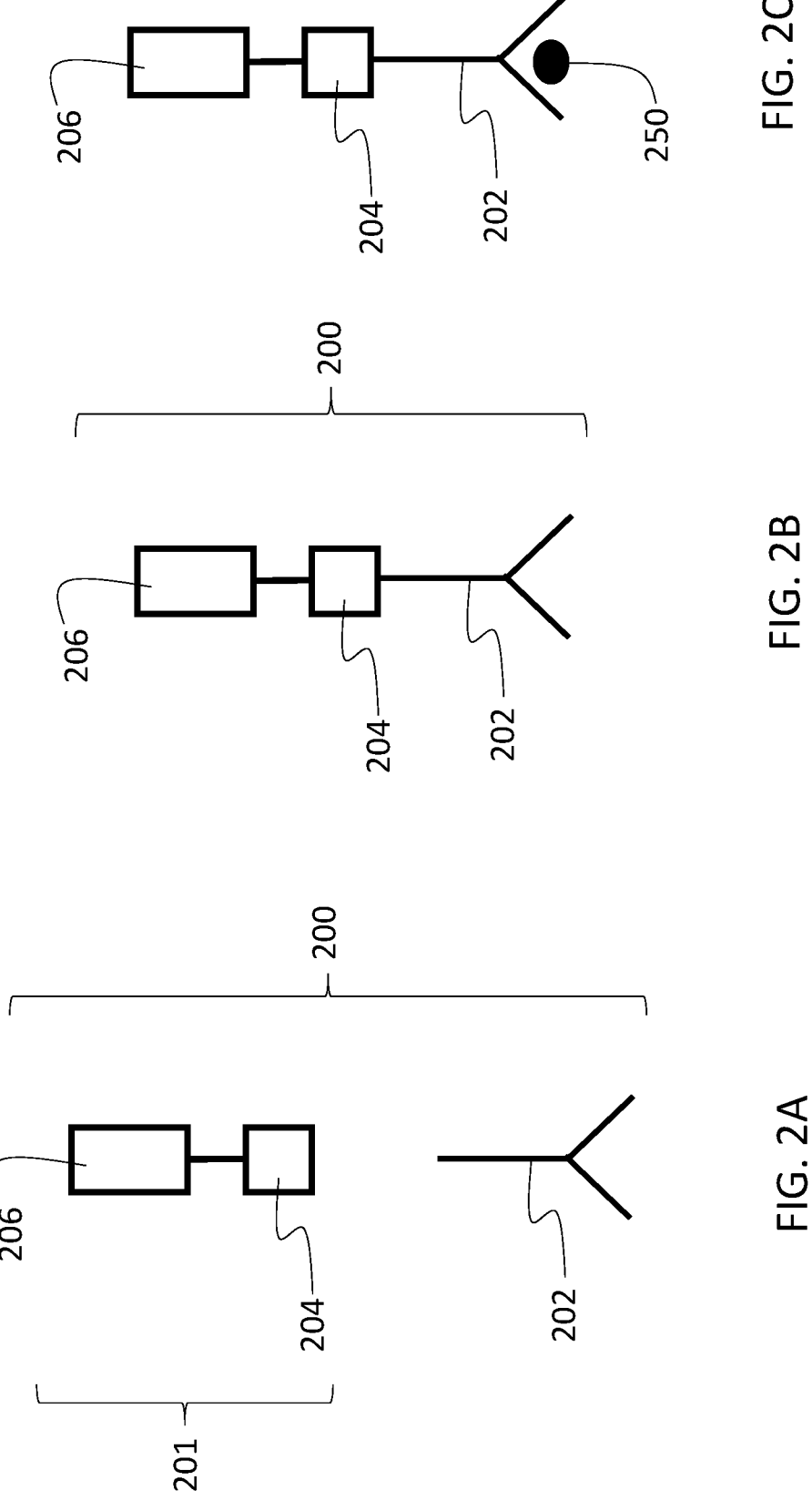
FIG. 2A is a schematic diagram showing components of an example probe.
FIG. 2B is a schematic diagram showing an example probe.
FIG. 2C is a schematic diagram showing an example probe bound to a target analyte in a biological sample.

FIG. 2A is a schematic diagram showing components of an example probe. Probe 200 in FIG. 2A includes a binding moiety 202 and a labeling moiety 201. Labeling moiety 201 includes a nanobody 204 linked to a labeling species 206. Typically, binding moiety 202 is a primary antibody or antibody fragment that specifically binds to a particular target analyte (i.e., a target protein, such as a target antigen) in the sample. Nanobody 204 of labeling moiety 201 in turn binds to a site on the antibody that is different from the target analyte-binding region of binding moiety 202. As such, conjugating nanobody 204 to binding moiety 202 does not disrupt the specificity or binding affinity of binding moiety 202.

FIG. 2B is a schematic diagram showing probe 200 after nanobody 204 is conjugated to binding moiety 202. As mentioned above, conjugation between labeling moiety 201 and binding moiety 202 can be performed either prior to or after binding moiety 202 is introduced into the sample. In some embodiments, for example, probe 200 is formed prior to introduction into the sample. To form probe 200 in such a manner, binding moiety 202 and labeling moiety 201 are simply incubated in a buffer solution, resulting in conjugation of nanobody 204 to binding moiety 202 to yield probe 200 as shown in FIG. 2B. Excess labeling moieties 201 that do not conjugate to binding moiety 202 can be removed by washing, or inactivated by binding to a scavenger material for which nanobodies 204 have binding affinity (e.g., rabbit IgG fragments), thereby rendering these labeling moieties inactive. Following this procedure, the probe solution contains few or no functionally active, unbound labeling moieties 201.

Alternatively, in certain embodiments, binding moiety 202 is first introduced into the sample, and selectively binds to a particular target analyte in the sample. Then, labeling moiety 201 is introduced into the sample, and nanobody 204 of labeling moiety 201 selectively conjugates to binding moiety 202, resulting in the in situ formation of probe 200.

Either of the foregoing methods of forming probe 200 results in a target analyte 250, as shown in FIG. 2C, that is labeled with probe 200 consisting of binding moiety 202 conjugated to nanobody 204, which is in turn linked to labeling species 206.

Typically, a sample contains multiple target analytes of interest, e.g., multiple different protein targets. To assay different protein targets, multiple different types of probes 200 are introduced into the sample. Each different type of probe includes a binding moiety (e.g., a primary antibody) that specifically binds to a particular target analyte, and labeling moiety conjugated to the binding moiety. The labeling moiety includes a nanobody that is conjugated to the binding moiety and a labeling species 206. In general, the labeling species 206 is uniquely associated with the binding moiety, and therefore, with the target analyte. That is, different types of probes targeting different analytes include different labeling species 206, which allows the different analytes to be detected in the sample.

When different types of probes are introduced into the sample, the probes can be formed prior to introduction into the sample, or in situ within the sample as described above. Further, certain probes can be formed prior to introduction into the sample and other probes can be formed in situ within the sample, depending upon the specific nature of the assay.

In general, the number of different types of probes that can be introduced into the sample according to any of the methods described above can be 1 or more (e.g., 2 or more, 3 or more, 4 or more, 5 or more, 6 or more, 8 or more, 12 or more, 16 or more, 20 or more, 30 or more, 40 or more, 50 or more, 60 or more, 70 or more, 80 or more, 100 or more, or even more).

A wide variety of different types of nanobodies 204 can be used in the methods described herein. In some embodiments, for example, nanobodies 204 are derived from one or more camelid species and include a single variable domain located on a heavy chain, i.e., $V_HH$ fragment nanobodies. In certain embodiments, nanobodies 204 are derived from one or more species of cartilaginous fish and are $V_{NAR}$ fragment nanobodies. Other nanobodies can also be used.

Many different combinations of binding moieties and nanobodies can be used in the methods described herein, and it should be understood that unless specifically described otherwise, the methods are not limited in any manner as to the types of binding moieties (e.g., primary antibodies) and types of nanobodies that can be used to form probes for specific target analytes. Nonetheless, specific examples are described below for further elucidation of the methods described herein.

In some embodiments, the binding moiety is a rabbit monoclonal antibody such as Abcam ab93278 (available from Abcam, Waltham, MA) with an Fab region that targets a particular antigen of interest, such as CD8 in human samples. A single-domain antibody, or nanobody, targeting species-specific IgG is conjugated to an oligonucleotide sequence that contains a barcode sequence. The nanobody binds to the primary antibody with high affinity. The probe that is formed localizes at a target CD8 domain in the sample based on the properties of the primary antibody. Imaging is performed by introducing a readout moiety conjugated to an oligo sequence that contains a countersense sequence to the barcode sequence associated with the nanobody.

In certain embodiments, the binding moiety is a mouse monoclonal antibody such as Abcam ab9475 (available from Abcam, Waltham, MA), with an Fab region that targets a particular antigen of interest, such as CD20 in human samples. A nanobody targeting mouse IgG2a is conjugated to an oligonucleotide that contains a barcode sequence. The nanobody binds to the primary antibody with high affinity. The probe that is formed localizes at a target CD20 domain in the sample based on the properties of the primary antibody. Imaging is performed by introducing a readout moiety conjugated to an oligo sequence that contains a countersense sequence to the barcode sequence associated with the nanobody.

In FIGS. 2A-2C, a single nanobody 204 is conjugated to a single binding moiety 202. More generally, however, one or more nanobodies 204 can bind to a single binding moiety 202. In some embodiments, each binding moiety 202 is conjugated to one or more (e.g., two or more, three or more, four or more, five or more, or even more) nanobodies 204. In certain embodiments, each of the nanobodies 204 conjugated to binding moiety 202 is of the same type (i.e., is linked to the same type of labeling species 206).

Figure 2D:
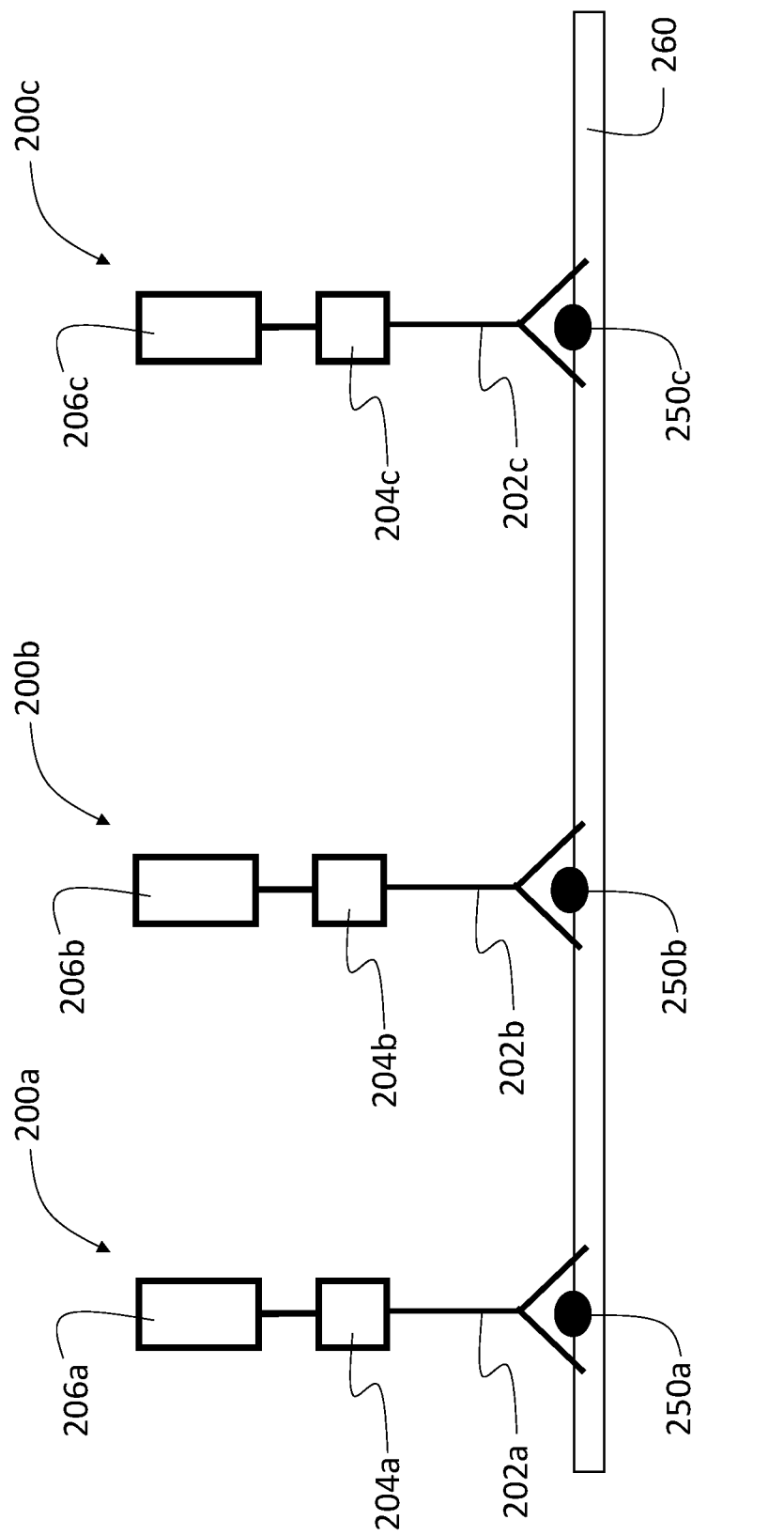
FIG. 2D is a schematic diagram showing examples of different probes bound to different target analytes in a biological sample.

FIG. 2D is a schematic diagram showing a sample 260 that includes different target analytes 250a-250c, each of which is labeled with a different type of probe 200a-200c. Probes 200a-200c contain binding moieties 202a-202c, nanobodies 204a-204c conjugated to the binding moieties, and labeling species 206a-206c linked to the nanobodies. The binding moieties, nanobodies, and labeling species shown in FIG. 2D can have any of the properties described herein in connection with these entities.

After sample 260 has been labeled as shown in FIG. 2D, one or more fixatives such as paraformaldehyde (PFA), methanol, or bissulfosuccinimidyl suberate (BS3) can optionally be applied to the sample in one or more fixation steps. Without wishing to be bound by theory, it is believed that this procedure crosslinks probes to the sample, and may crosslink nanobodies to the detection moieties to which they are conjugated. The overall effect is to reduce or eliminate migration of probes and nanobodies to other sites.

A number of practical factors related to common antibodies may affect the methods, probes, and kits described herein. Many antibodies are raised against rabbit or mouse hybridomas. In certain applications, such as diagnostic testing, monoclonal antibodies are preferred. Mouse antibodies consist of five isotypes: IgG1, IgG2a, IgG2b, IgG2c, and IgG3, which can be used as targets for nanobody attachment. Rabbit IgG has only one isotype.

Antibodies are routinely made using recombinant techniques. In some embodiments, the amino acid sequence is altered so the resulting antibody contains different amino acids in the Fc region than the original antibody while still targeting the same sample compound at its Fab region. This enables use of antibodies that target the same antigen but contain a different, selected site for labeling.

Similarly, nanobodies can be made using recombinant techniques. For example, a set of anti-mouse and anti-rabbit IgG secondary $V_H$H nanobodies, and the sequences for making them using recombinant methods, is described in Pleiner et al., *J. Cell Biol.* 217(3): 1143-1154 (2017), the entire contents of which are incorporated herein by reference.

In general, a nanobody binds to a detection moiety (e.g., a primary antibody) with a dissociation constant $K_d$. In principle, a bound nanobody can dissociate from a detection moiety to which it is bound and remain unbound in the sample, or bind to another antibody in the sample. If nanobody migration in this manner occurs with sufficiently high frequency, an image of the sample will report target analyte molecules in the sample as being the wrong type of analyte.

To reduce and/or prevent nanobody dissociation and migration from one binding moiety to another, in some embodiments, the nanobodies and binding moieties are selected such that for one or more nanobody-binding moiety pairs (or even for all nanobody-binding moiety pairs) that are introduced into the sample, the dissociation constant $K_d$ is $5.0 \times 10^{-9}$ mol/L or less (e.g., $1.0 \times 10^{-9}$ mol/L or less, $5.0 \times 10^{-10}$ mol/L or less, $1.0 \times 10^{-10}$ mol/L or less, $5.0 \times 10^{-11}$ mol/L or less, $1.0 \times 10^{11}$ mol/L or less, $1.0 \times 10^{-12}$ mol/L or less, or even less). When $K_d$ is sufficiently low, the number of free nanobody labeling moieties in the sample is low, and migration of nanobody labeling moieties from one probe to another is not a barrier to multiplexed imaging.

In some embodiments, labeling species 206 contains an optical moiety that generates an optical signal that can be detected. Examples of optical moieties will be discussed in greater detail subsequently. In these embodiments, labeling target analytes with probes (step 102 in FIG. 1) also results in exposure of the sample to optical labels (step 104 in FIG. 1), and signals arising from the optical labels are then measured directly (step 106 in FIG. 1).

In certain embodiments, labeling species 206 contains an oligonucleotide. In general, the oligonucleotide includes multiple nucleotides. The nucleotides can include, for example, DNA bases (e.g., A, C, G, T), RNA bases (e.g., A, C, G, U), and any combination for DNA and/or RNA bases. The oligonucleotide can also include non-natural (e.g., synthetic) nucleotides, including DNA analogues and/or RNA analogues. Examples of such synthetic analogues include, but are not limited to, peptide nucleic acids, morpholino and locked nucleic acids, glycol nucleic acids, and threose nucleic acids.

The sequence of bases in the oligonucleotide can generally be any sequence. Moreover, in general, nucleotides and other moieties in the oligonucleotide can be conjugated via natural and/or non-natural (e.g., synthetic) linkages.

In some embodiments, the oligonucleotide includes one or more nucleotides that are capable of base pairing with high reliability with a complementary nucleotide. Examples of such nucleotides include, but are not limited to, 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine, and 2-thio-uridine.

In certain embodiments, the oligonucleotide can correspond to, or contain one or more fragments of, specialized nucleic acid species. For example, the oligonucleotide can correspond to, or contain one or more fragments of, a locked nucleic acid (LNA), a peptide nucleic acid (PNA), an unlocked nucleic acid (UNA), and/or a morpholino oligomer.

The length of the oligonucleotide (e.g., the number of nucleotides in the oligonucleotide) can generally be selected as desired to ensure efficient and selective hybridization interactions. In some embodiments, the oligonucleotide can include at least 5 (e.g., at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100) nucleotides.

In some embodiments, the oligonucleotide can have between 5-30, between 5-25, between 5-20, between 10-20, between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides.

In certain embodiments, the oligonucleotide can have no more than 5 (e.g., no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100) nucleotides.

In some embodiments, the oligonucleotide can be fully single stranded. Alternatively, in certain embodiments, the oligonucleotide can be at least partially double stranded. A partially double stranded region of the oligonucleotide can be at the 3' end of the oligonucleotide, at the 5' end of the oligonucleotide, or between the 5' end and 3' end of the oligonucleotide.

As shown in FIGS. 2A-2C, the oligonucleotide (e.g., labeling species 206) is linked to nanobody 204. In general, site-specific labeling techniques can be used to conjugate oligonucleotides to nanobodies at a selected number of known locations. Such methods are described, for example, in Gong et al., *Bioconjugate Chem.* 27(1): 217-225 (2016), in Sograte-Idrissi et al., *Cells* 8(1): 48 (2019), in Bernardinelli at al., *New Biotechnology* 56: 1-8 (2020), and in Wiener et al., *Scientific Reports* 10: 1457 (2020), the entire contents of each of which are incorporated by reference herein.

Figures 3, 4:
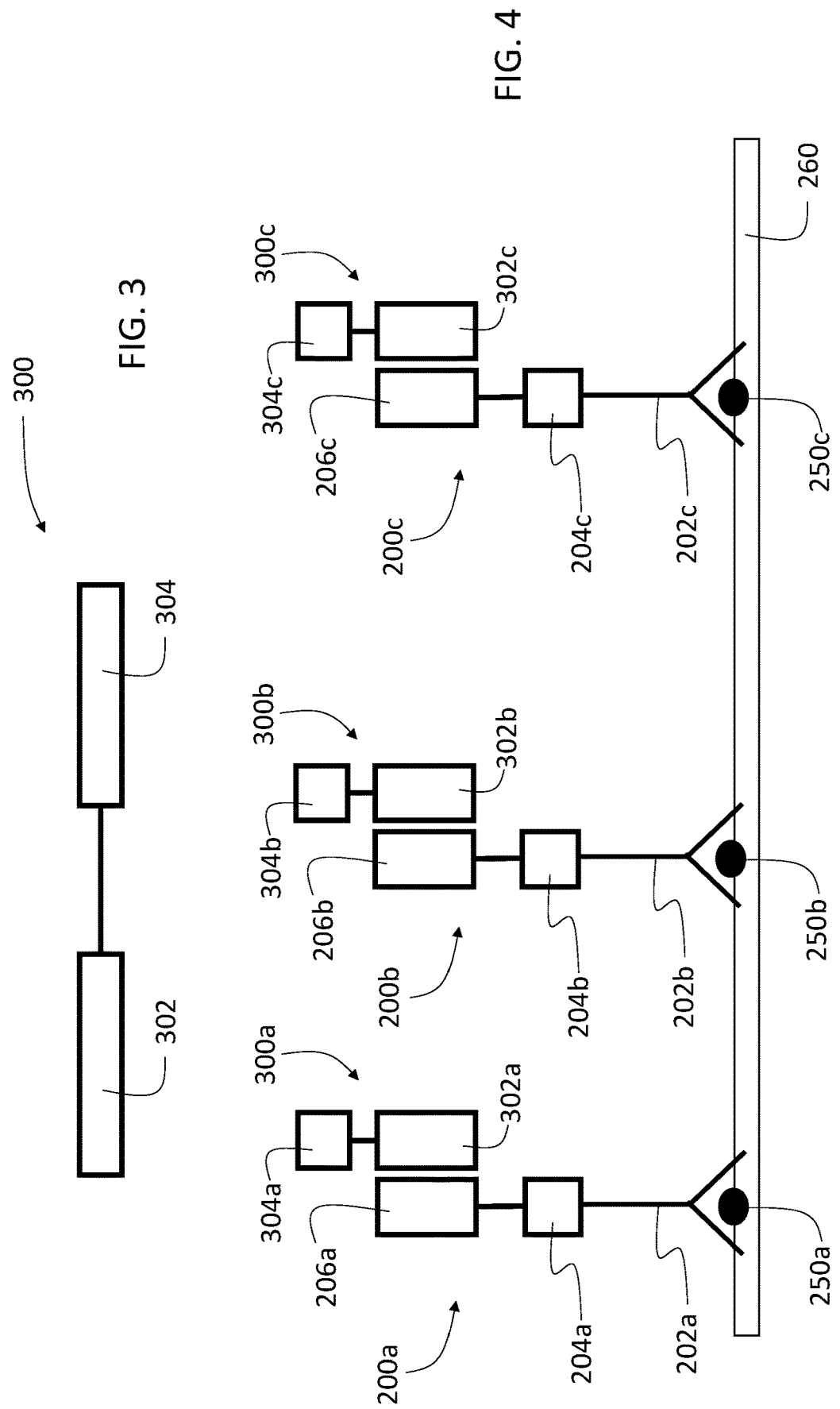
FIG. 3 is a schematic diagram showing an example of an optical label.
FIG. 4 is a schematic diagram showing examples of different optical labels hybridized to different probes in a biological sample.

Returning to FIG. 1, after labeling of the target analytes with probes in step 102, the sample is exposed to a set of optical labels in step 104. FIG. 3 is a schematic diagram of an example optical label 300 that includes an oligonucleotide 302 and an optical moiety 304. Other moieties and structural features can optionally be present in optical label 300.

Oligonucleotide 302 can generally include any of the features described herein for the oligonucleotide of labeling species 206. Oligonucleotide 302 can, in some embodiments, include the same number of nucleotides as the oligonucleotide of labeling species 206. Alternatively, in certain embodiments, oligonucleotide 302 can include a different number of nucleotides.

Oligonucleotide 302 can have the same or different strand structure as the oligonucleotide of labeling species 206. That is, oligonucleotide 302 can be single stranded, double stranded, or partially double stranded, irrespective of the structure of the oligonucleotide of labeling species 206. Oligonucleotide 302 can generally include any number of double stranded regions, as described above for the oligonucleotide of labeling species 206, extending over a portion of the total length of oligonucleotide 302.

When introduced into the sample, oligonucleotide 302 hybridizes to the oligonucleotide of labeling species 206 via base pairing so that probe 200 and optical label 300 are co-localized in the sample at the location of the target analyte, as shown in FIG. 4. The efficiency of hybridization is related in part to the extent of complementarity between the sequences of the oligonucleotides. As used herein, the percentage to which the sequences of the two sequences are complementary refers to the percentage of nucleotides in the shorter of the two sequences that have a complementary counterpart at a complementary location in the other sequence, such that the two counterparts pair during hybridization. In some embodiments, for example, the sequences of the two oligonucleotides are at least 70% (e.g., at least 75%, at least 80%, at least 85%, at least 90%, at least 95%, at least 99%) complementary.

As used herein, the term "at least partially complementary" means that two nucleotide sequences are sufficiently complementary that they hybridize. In general, two nucleotide sequences are at least partially complementary if their sequences are at least 50% complementary.

In general, oligonucleotide 302 includes at least one binding region that hybridizes to a corresponding binding region of the oligonucleotide of labeling species 206. The binding region can be located at the 3' end, at the 5' end, or intermediate between the two ends, of oligonucleotide 302. Where oligonucleotide 302 includes multiple binding regions, any of the binding regions can be located as above.

In some embodiments, the binding region of oligonucleotide 302 is at least partially complementary to, and hybrid-izes with, the 3' end of the oligonucleotide of labeling species 206. In certain embodiments, the binding region of oligonucleotide 302 is at least partially complementary to, and hybridizes with, the 5' end of the oligonucleotide of labeling species 206.

In certain embodiments, the binding region of oligonucleotide 302 is at least partially complementary to, and hybridizes with, an intermediate region of the oligonucleotide of labeling species 206. In some embodiments, the binding region of oligonucleotide 302 is at least partially complementary to, and hybridizes with, the entire oligonucleotide of labeling species 206. In certain embodiments, the binding region of the oligonucleotide of labeling species 206 is at least partially complementary to, and hybridizes with, the entire oligonucleotide 302.

In certain embodiments, one or both of the oligonucleotides include(s) multiple binding regions separated by one or more non-binding regions. In general, each of the binding regions can have any of the properties discussed above in connection with the oligonucleotides and their respective binding regions.

Non-binding regions in the oligonucleotides can be formed by and/or include a variety of different linking species, including non-complementary nucleotide sequences and spacer moieties that do not include nucleotides. Non-binding regions can have the same or different geometric lengths, and binding regions can have the same or different lengths (e.g., the same or different numbers of nucleotides). Within each oligonucleotide, binding regions and non-binding regions can have the same or different lengths.

In some embodiments, detection moiety 202 can be conjugated to multiple labeling species 206 in probe 200, i.e., via conjugation of multiple labeling moieties 201 to a single detection moiety 202 and/or via a labeling moiety 201 that includes multiple labeling species 206, each of which is the same. Where labeling species 206 is an oligonucleotide, each of the multiple oligonucleotides associated with detection moiety 202 can have the same nucleotide sequence, so that the oligonucleotide 302 can hybridize with any of the oligonucleotides of probe 200. In general, 2 or more (e.g., 3 or more, 4 or more, 5 or more, 6 or more, 7 or more, 8 or more, or even more) oligonucleotides having the same sequence can be present in probe 200. In this manner, additional optical labels can be selectively located in the sample at the location of the target analyte, thereby enhancing the measurement of detection signals from the sample that correspond to the target analyte.

In general, optical label 300 includes one or more optical moieties 304. In FIG. 3, optical label 300 includes a single optical moiety 304 linked to oligonucleotide 302 for purposes of discussion. More generally, however, optical label 300 can include 1 or more (e.g., 2 or more, 3 or more, 4 or more, 5 or more, 6 or more, 8 or more, 10 or more, or even more) optical moieties 304 linked to oligonucleotide 302.

A variety of different optical moieties 304 can be used, depending upon the nature of the methodology used to identify and quantify target analytes in the sample. In some embodiments, for example, optical moiety 304 includes a dye. As used herein, a "dye" is a moiety that interacts with incident light, and from which emitted light can be measured and used to detect the presence of the dye in a sample. In general, a dye can be a fluorescent moiety, an absorptive moiety (e.g., a chromogenic moiety), or another type of moiety that emits light, and/or modifies incident light passing through or reflected from a sample where the dye is present so that the presence of the dye can be determined by measuring changes in transmitted or reflected light from the sample.

In certain embodiments, the optical moiety can include a hapten. The hapten can subsequently (or concurrently) be bound to a dye moiety to provide an optical moiety that can be detected by measuring emitted, transmitted, or reflected light from the sample.

When the optical moiety of optical label 300 includes a dye, a wide variety of different dyes can be used. For example, the dye can be a xanthene-based dye, such as a fluorescein dye and/or a rhodamine dye. Examples of suitable fluorescein and rhodamine dyes include, but are not limited to, fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110.

The dye can also be a cyanine-based dye. Suitable examples of such dyes include, but are not limited to, the dyes Cy3, Cy5 and Cy7. The dye can also be a coumarin dye (e.g., umbelliferone), a benzimide dye (e.g., any of the Hoechst dyes such as Hoechst 33258), a phenanthridine dye (e.g., Texas Red), an ethidium dyes, an acridine dyes, a carbazole dye, a phenoxazine dye, a porphyrin dye, a polymethine dye (e.g., any of the BODIPY dyes), and a quinoline dye.

When the dye is a fluorescent moiety, the dye can be a moiety corresponding to any of the following non-limiting examples and/or derivatives thereof: pyrenes, coumarins, diethylaminocoumarins, FAM, fluorescein chlorotriazinyl, fluorescein, Rl 10, JOE, R6G, tetramethylrhodamine, TAMRA, lissamine, napthofluorescein, Texas Red, Cy3, and Cy5.

In certain embodiments, the dye can include one or more quantum dot-based species. Quantum dot-based fluorophores are available with fluorescence emission spectra in many different spectral bands, and suitable quantum dot-based dyes can be used as labeling species in the methods described herein.

As shown in FIG. 3, oligonucleotide 302 and optical moiety 304 are linked in optical label 300. In general, the linkage between oligonucleotide 302 and optical moiety 304 can correspond to any of a variety of different linkages, including direct covalent bonds and conjugation via linking moieties such as aliphatic and/or aromatic linking species (e.g., $C_{1-20}$ cyclic and non-cyclic alkyl species, $C_{2-20}$ cyclic and non-cyclic alkene species, $C_{2-20}$ cyclic and non-cyclic alkyne species, and $C_{3-24}$ aromatic species, optionally including heteroatoms such as, but not limited to, O, S, N, and P, and optionally including one or more substituents selected from the group consisting of: halide groups; nitro groups; azide groups; hydroxyl groups; primary, secondary, and tertiary amine groups; aldehyde groups; ketone groups; amide groups; ether groups; ester groups; thiocyanate groups; and isothiocyanate groups).

In some embodiments, the linkage between oligonucleotide 302 and optical moiety 304 is provided by a pair of binding partners. In general, any pair of binding partners can be used. One example of a pair of binding partners is streptavidin and biotin. In certain embodiments, for example, optical label 300 can be introduced by first contacting the sample with a oligonucleotide 302 linked to a first binding partner of a binding partner pair (e.g., streptavidin or biotin). Next, the optical label 300 can be completed contacting the sample with an optical moiety 304 linked to the second binding partner of the binding partner pair (e.g., biotin or streptavidin). The two binding partners bind, forming the linkage between oligonucleotide 302 and optical moiety 304, and completing the addition of optical label 300 to the sample.

Biological samples typically include multiple analytes of interest, and as described above, the methods and kits discussed herein can be used to perform multiplexed labeling and detection of target analytes. FIG. 4 is a schematic diagram of a sample 260 that includes three different types of target analytes 250a-250c. The different types of target analytes can each independently be any of the different types of target analytes described herein. In some embodiments, for example, the different types of target analytes can be different proteins, antigens, peptides, or other amino acid-containing species. In some embodiments, the different types of target analytes can include combinations of any of the different types of target analytes described herein (e.g., proteins, antigens, peptides, and amino acid-containing species).

To detect and optionally quantify each of the different types of target analytes in sample 260, the sample is exposed to optical labels 300a-300c that selectively hybridize, respectively, to probes 200a-200c in the sample (introduced in step 102 of FIG. 1). Probes 200a-200c can each independently have any of the properties discussed herein in connection with probe 200. Each of probes 200a-200c selectively binds to only one type of target analyte 250a-250c, so that each type of target analyte in sample 260 is bound to a different type of probe.

As discussed above, an important aspect of probes 200a-200c is that in general, the labeling species 206a-206c of probes 200a-200c differ. In particular, where the labeling species 206a-206c are oligonucleotides, the nucleotide sequences of the oligonucleotides differ. This allows each of the probes 200a-200c to be selectively associated with a different optical label 300a-300c for detection. As such, different optical labels can be localized in the sample at locations corresponding to the different target analytes 250a-250c, allowing each of the target analytes to be separately identified and quantified.

To detect target analyte 250c for example, the sample is contacted with optical label 300c, which includes oligonucleotide 302c and optical moiety 304c. As shown in FIG. 4, oligonucleotide 302c is complementary to the oligonucleotide of labeling species 206c of probe 200c, so that oligonucleotide 302c selectively hybridizes to the oligonucleotide of labeling species 206c, but not to the oligonucleotides of labeling species 206a or 206b. As a result, optical label 300c associates/binds selectively with probe 200c in sample 260, and is spatially localized in sample 260 only where target analyte 202c is located.

Following binding of optical label 300c to probe 100c, an optical signal arising from optical label 300c is measured (e.g., a fluorescence emission signal). Measurement of such signals can be performed, for example, by obtaining an image of sample 260. The measured optical signal indicates the presence of optical label 300c—and therefore target analyte 250c—at specific locations within the sample, allowing for spatially resolved identification of the target analyte. Further, by measuring the intensity of the optical signal at different locations within the sample (e.g., the spatially-resolved fluorescence emission intensity at specific pixel locations within an image of the sample), the amount of the target analyte at specific locations in the sample can be quantified.

After the optical signal arising from optical label 300c has been measured, target analytes 250a and/or 250b can also be identified and/or quantified in sample 260. To identify these target analytes, optical label 300c is typically (but optionally) first removed from sample 260 by dehybridization or another method, or inactivated in sample 260. Dehybridization can be accomplished using various methods including, but not limited to: exposure to one or more chaotropic reagents; thermally-induced dehybridization via heating; toehold mediated strand displacement (TMSD); and enzymatic strand displacement using enzymes such as RNAse, DNAse.

In certain embodiments, optical labels (or portions of optical labels) can be removed from sample 260 using one or more reducing agents that cleave covalent bonds that link an optical moiety to an oligonucleotide in an optical label. The cleaved optical moieties can then be washed from the sample. The oligonucleotides can optionally remain hybridized to probes in the sample. A variety of different reducing agents can be used for this purpose. For example, tri(2-carboxyethyl)phosphine (TCEP) can be used to cleave optical moieties that are linked via disulfide bonds to oligonucleotides in optical labels.

In some embodiments, optical labels are not removed from the sample, but are instead inactivated so that they do not generate optical signals in subsequent detection cycles. Various methods can be used for inactivation of optical labels. For example, in certain embodiments, chemical bleaching can be used to inactivate optical labels.

After optional removal of label 300c, sample 260 is contact with optical labels that selectively associate with probes 200a and 200b, respectively, in the manner discussed above, to selectively localize these optical labels in the sample at locations corresponding to target analytes 250a and 250b, respectively. Optical signals measured from the sample that correspond to the localized optical labels can then be used to identify and/or quantify target analytes 250a and 250b in a spatially-resolved manner within sample 260.

When the sample contains multiple target analytes of interest, as discussed above, the target analytes (e.g., target analytes 250a-250c) can be contacted with different types of probes (e.g., probes 200a-200c), where each type of probe in the set selectively binds to one of the different types of target analytes. Then, referring again to step 104 in FIG. 1, the different types of probes are associated with different corresponding optical labels, and measurement signals for the corresponding types of target analytes bound to the probes are detected.

For a sample that contains a relatively large number of target analytes, the analysis can be performed in multiple analysis cycles. Each analysis cycle involves contacting the sample with a set of one or more different types of optical labels. Where more than one type of optical label is present in the set, each different types of optical label selectively associates with a different type of probe (and therefore, with a different type of analyte). Provided that the optical moieties of the optical labels are different, a multispectral image of the sample contains distinguishable contributions from the optical moieties. These contributions can be separated computationally and used to identify and/or quantify the multiple different types of analytes in a spatially-localized manner within the sample in each cycle.

Accordingly, in step 104 as described above, the sample is exposed to a set of one or more optical labels 300. The set of optical labels typically includes between 1 and 8 different optical labels (e.g., two, three, or four different optical labels), but can generally include any number of optical labels in each cycle of the flow chart of FIG. 1. Each type of optical label includes a different type of oligonucleotide 302. For a particular type of optical label, if oligonucleotide 302 of the optical label is complementary to the oligonucleotide of labeling moiety 206 of one of the types of probes in the sample, the oligonucleotides hybridize, associating the optical label with the probe, such that the optical label is localized in the sample at locations where the target analyte to which the type of probe is bound is located. As such, different target analytes within each cycle of the flow chart can be labeled with different optical moieties, and can be identified based on measured optical signals that correspond to the different optical moieties.

To increase the efficiency with which different types of target analytes are identified (e.g., by reducing the number of detection cycles), the set of optical labels can be selected such that, for at least one (and generally, more than one) cycle, multiple different optical labels of the introduced set each selectively associate with one of the different probe types, and generate optical signals. In this manner, multiple types of target analytes can be identified in a single detection cycle, reducing the number of cycles required to fully elucidate all of the target analytes present in the sample. By selecting the optical label set in each cycle such that each of multiple different optical labels selectively associates with one of the different types of probes in the sample, the number of detection cycles can be more efficiently utilized to identify the different types of probes, and therefore, the different target analytes in the sample.

Next, in step 106, optical signals corresponding to the optical labels are measured. In some embodiments, the optical signals are measured by obtaining one or more images (e.g., multispectral images) of the sample. To obtain the one or more images, the sample is exposed to incident light, and signal radiation generated by the optical labels (e.g., fluorescence emission) is detected using an imaging detector such as a CCD array or CMOS-based array detector.

In general, each of the different optical labels in the sample generates signal radiation according to a different spectral distribution, and is therefore associated with a different detection channel. In practice, signal radiation in different detection channels can be detected in a variety of ways. In some embodiments, where each detection channel is well separated spectrally from the other detection channels, the signal radiation generated by each different type of optical label is relatively well isolated spectrally in a distinct detection channel. As such, signal radiation attributable to each of the different types of optical labels can readily be isolated and detected by spectral filtering (e.g., with a plurality of optical bandpass filters) and/or by using a spectrally resolving detector, such as a grating, prism, or other spectrally dispersive element in conjunction with a CCD array or CMOS-based array detector.

In certain embodiments, the spectral distributions of signal radiation generated by the different optical labels may overlap to a degree that is not insignificant, such that optical filtering and spectral dispersion methods alone are insufficient to isolate signal radiation generated by each of the different labeling agents or optical labels. Because the spectral distributions of the signal radiation are spectrally convolved to some extent, accurate detection of signals generated by each of the optical labels may therefore involve more complex spectral deconvolution techniques to accurately separate and assign measured signals to specific labeling agents or optical labels.

In such circumstances, sample images that include signal radiation from multiple different optical labels can optionally be decomposed into a set of images, in which each image in the set corresponds substantially only to signal radiation from one optical moiety. A variety of methods can be used to perform such decompositions, including for example spectral unmixing methods that involve performing an eigenvector decomposition of the measured optical signals into individual contributions from "pure" spectral components (e.g., contributions from each optical label). Methods for spectral unmixing are described, for example, in U.S. Pat. Nos. 10,126,242 and 7,555,155, and in PCT Patent Publication No. WO2005/040769, the entire contents of each of which are incorporated herein by reference.

Step 106 yields a set of one or more images of the sample. Particular pixels at a common location in the set of images correspond to the same location in the sample, which is represented by the common pixel location in the images. Collectively, pixels across the set of images that correspond to a common pixel location are associated with optical signals generated by optical labels at the corresponding location in the sample. Because the optical signals generated by each different type of optical label in a detection cycle are known, the presence or absence of each type of target analyte in the sample at each pixel location can be determined. Further, the measured intensities of optical signals corresponding to the different types of target analytes at each pixel can be used to quantify the amount of each type of target analyte in a spatially-resolved manner within the sample.

Following step 106, the set of optical labels can optionally be inactivated or removed from the sample in step 108. A variety of different methods can be used in step 108 for removal or inactivation of optical labels, as described above.

Next, in step 110, if analysis of the target analytes present in the sample is complete, then the workflow ends. However, if analysis is not complete, one or more additional cycles of steps 104, 106, and 108 are performed. In each additional cycle, a set of optical labels is optionally introduced into the sample, optical signals corresponding to the optical labels are measured and optionally decomposed as described above, and the optical labels can optionally be inactivated or removed from the sample. The workflow shown in FIG. 1 can be repeated for any number of cycles to detect and quantify target analytes in the sample.

Additional aspects of the methods for labeling and identifying target analytes in biological samples are described in PCT Patent Publication No. WO 2020/163397, in U.S. Provisional Patent Application No. 63/229,064, and in U.S. Pat. No. 10,370,698, the entire contents of each of which are incorporated by reference herein.

Signal Amplification Via Enzyme-Mediated Deposition of Optical Labels

The nanobody-based probes described herein can also be used in connection with enzyme-mediated deposition of optical moieties in samples for labeling of target analytes, and in particular, for labeling individual target analyte molecules with more than one optical moiety. The effect of this type of labeling is to achieve amplification of measurement signals corresponding to the target analytes.

Figure 5:
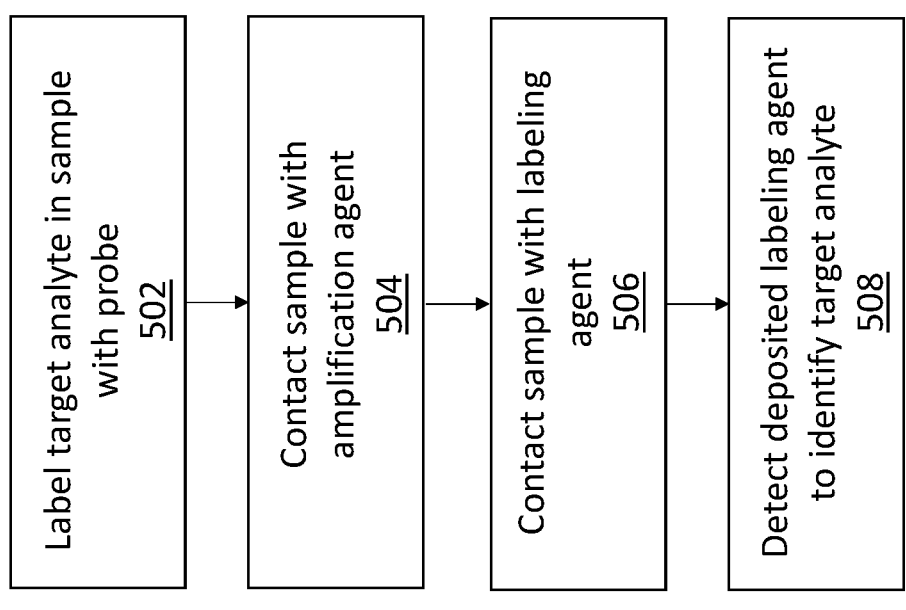
FIG. 5 is a flow chart showing a set of example steps for depositing a labeling agent in a biological sample in proximity to a target analyte.

FIG. 5 is a schematic diagram showing a set of example steps for amplifying detection signals corresponding to target analytes with the nanobody-based probes described herein. In a first step 502, a sample that includes a target analyte is labeled with a nanobody-based probe (e.g., probe 200) that specifically binds to the target analyte. This first step is illustrated schematically in FIG. 6A, where probe 200 specifically localizes at positions in the sample that correspond to target analyte 250. In general, any of the methods described above for labeling a sample with a nanobody-based probe 200 can be used in step 502.

In particular, in some embodiments, probe 200 can be formed by conjugating a binding moiety 202 with a labeling moiety 201 that includes a nanobody 204 linked to a labeling species 206. Conjugation can be performed external to the sample (e.g., via incubation), and then the probe 200 can be introduced into the sample to label target analyte 250. Alternatively, in certain embodiments, probe 200 can be formed in situ in the sample by first contacting sample 260 with binding moiety 202 to bind target analyte 250, and then contacting sample 260 with labeling moiety 201 to conjugate binding moiety 202 to nanobody 204, thereby forming probe 200 bound to target analyte 250.

Returning to FIG. 5, in a next step 504, the sample is contacted with an amplification agent 270 that associates with probe 200. As used herein, the terms "contacts" and "contacting" mean that an agent, species, moiety, or other element is brought into association with a sample, or another agent, species, moiety, or element, such that the two interact with one another. For example, when a sample is "contacted" with an agent, the sample is brought into close enough association with the agent that they interact. The agent can, for example, bind with the sample or with other agents, species, moieties, and/or elements that have previously been contacted to, bound to, hybridized to, and/or deposited in, the sample.

Figure 6B:
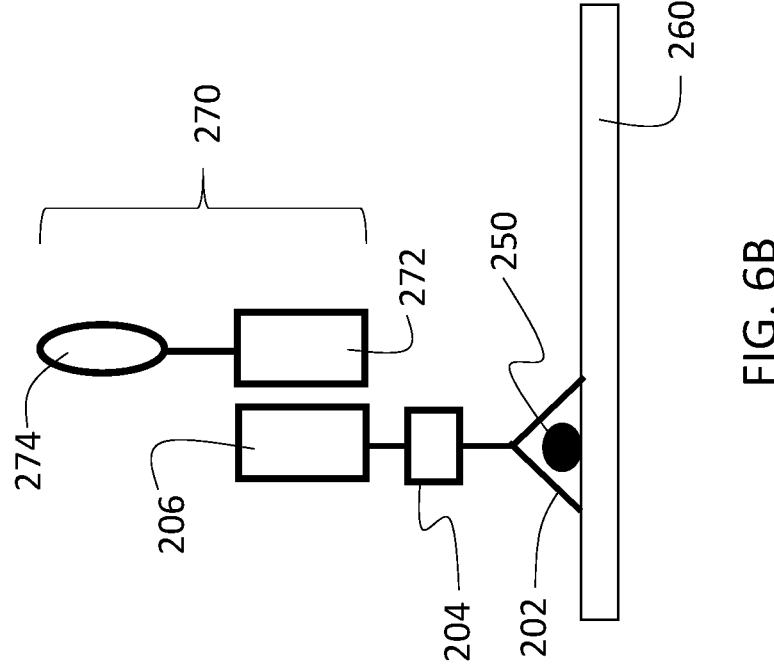
FIG. 6B is a schematic diagram showing an example of an amplification agent hybridized to a probe in a biological sample.
Figure 6A:
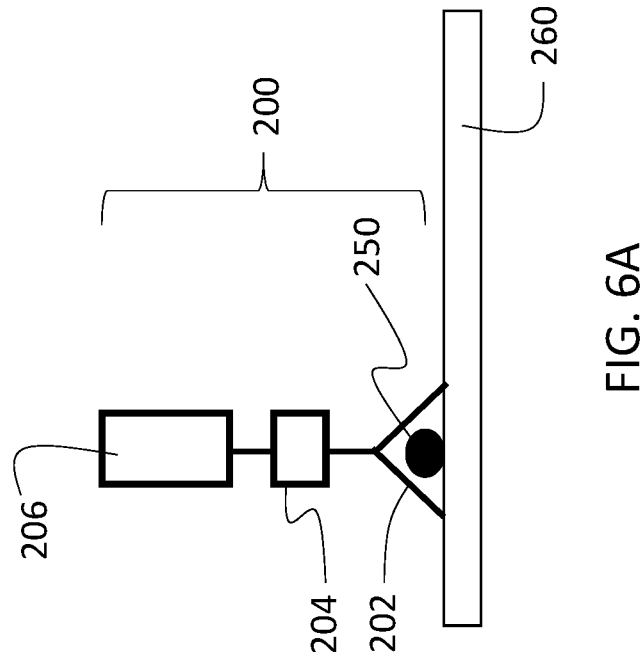
FIG. 6A is a schematic diagram showing an example of a probe bound to a target analyte in a biological sample.

Step 504 is illustrated schematically in FIG. 6B. In FIG. 6B, amplification agent 270 contacts sample 250. Amplification agent 270 includes an oligonucleotide 272 conjugated to a reactive species 274. Labeling species 206 of probe 200 contains an oligonucleotide as described above, and oligonucleotide 272 of amplification agent 270 is at least partially complementary to the oligonucleotide of labeling species 206, so that the oligonucleotides hybridize. In this manner, amplification agent 270 localizes in the sample at the same positions as probe 200, and therefore, at the positions corresponding to target analyte 250.

Returning again to FIG. 5, in step 506, the sample is contacted with a labeling agent. The labeling agent reacts with the reactive species of the amplification agent introduced in step 504, depositing the labeling agent (or a reaction product derived from the labeling agent) in the sample at locations in proximity to the amplification agent.

Figure 6C:
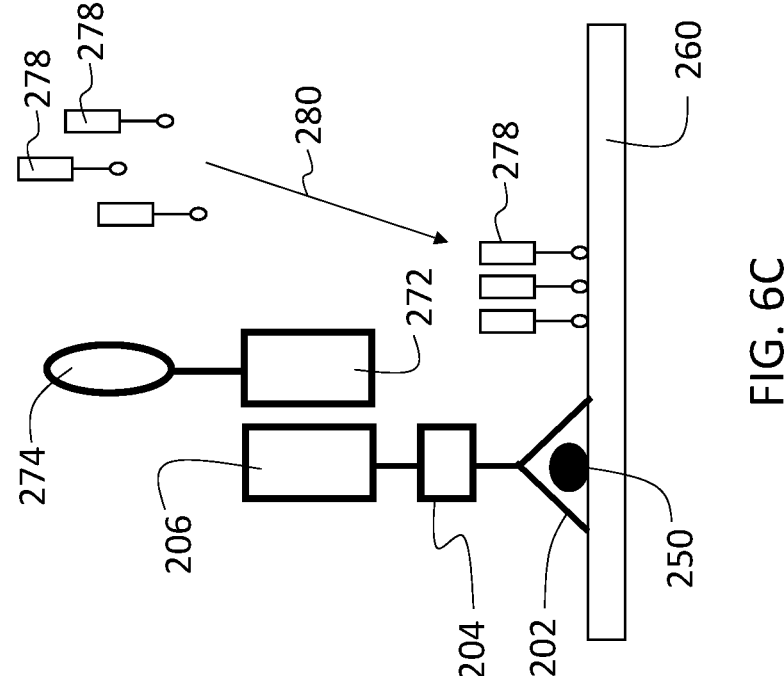
FIG. 6C is a schematic diagram showing deposition of a labeling agent in proximity to a target analyte in a biological sample.

This step is illustrated schematically in FIG. 6C, in which a labeling agent 278 contacts the sample. As shown in FIG. 2C, labeling agent 278 reacts with reactive species 274 in a reaction represented by arrow 280. The reaction deposits labeling agent 278 or a derivative thereof (e.g., a product of the reaction between labeling agent 278 and reactive species 274) in the sample at locations in proximity to the amplification agent 270, and therefore, at locations in proximity to target analyte 250. In this manner, the deposited labeling species 278 (or a reaction product thereof) is spatially co-localized with target analyte 250.

Again referring to FIG. 5, after deposition of the labeling species or a derivative thereof in step 506, the labeling species (or reaction product thereof) is detected in step 508 to identify and/or quantify target analyte 250 in sample 262.

In general, labeling species 278 includes at least one optical moiety. A variety of different optical moieties can be used, depending upon the nature of the methodology used to identify and quantify the target analyte. Labeling species

278 can typically include any one or more of the different types of optical moieties 304 described above.

Reactive species 274 in amplification agent 270 can correspond to any one or more of a variety of different chemical or biochemical species and moieties. In some embodiments, for example, reactive species 274 corresponds to a catalytic agent that catalyzes a reaction of labeling agent 278. Examples of catalytic agents that can correspond to reactive species 274 include, but are not limited to, enzymes, transition metal-based organometallic moieties, peroxide containing moieties, and photoactivatable species. Examples of suitable enzymes include, but are not limited to, horseradish peroxidase (HRP) and soybean peroxidase. In some embodiments, reactive species 274 can include a hemin-containing complex which can mimic HRP, such as hematin.

In some embodiments, reactive species 274 is an enzyme that participates an enzyme-mediated reaction to deposit labeling agent 278 (or a reaction product thereof) at locations in the sample that are proximate to amplification agent 270 and, therefore, to target analyte 250. As an example of enzyme-mediated deposition of a labeling species, reactive species 274 can be horseradish peroxidase (HRP) or another species that mimics the activity of HRP. HRP can be used in the methods described herein as a catalytic agent for tyramide signal amplification (TSA).

To implement TSA, labeling agent 278 includes an optical moiety (such as a dye, as described above) conjugated to a tyramide species. When sample 260 is initially contacted with labeling agent 278, the tyramide species is in an inactive form. However, HRP catalyzes conversion of the tyramide species to an active form that is capable of binding with sample 260. Following conversion of the tyramide species to its active form, the labeling agent binds to sample 260 at locations proximate to where it is generated (e.g., at the location of amplification agent 270 and target analyte 250). FIG. 6C illustrates schematically the deposition of labeling agent 278 (which can include an active tyramide species conjugated to an optical moiety) at locations in proximity to target analyte 250.

By adjusting the amount of tyramide-containing labeling agent 278 introduced into sample 260 and the amount of time during which the enzyme-mediated activation process continues, the amount of labeling agent 278 deposited in sample 260 can be controlled. As a result, the signal that is detected and that corresponds to labeling agent 278 (and therefore, to target analyte 250) can be "amplified". In the context of the present disclosure, amplification refers to the association of more than one labeling agent 278 molecule to a molecule of target analyte 250. With reference to immunohistochemical labeling methods in which each binding antibody is conjugated to a single fluorophore molecule, the TSA technique can be used to deposit multiple labeling agent 278 molecules (or derivatives thereof) in the sample to generate measurable signals corresponding to a single molecule of target analyte 250, thereby increasing the amplitude or intensity of measured signals corresponding to the single target analyte relative to signals that would otherwise be measured from a single labeling species.

In general, a ratio of the number of labeling agent 278 molecules that can be deposited in the sample in proximity to a single molecule of target analyte 250 is increased beyond 1:1 by implementing the TSA methodology described above. In some embodiments, for example, the ratio is 2:1 or more (e.g., 3:1 or more, 4:1 or more, 5:1 or more, 6:1 or more, 8:1 or more, 10:1 or more, 20:1 or more, 30:1 or more, or even more).

Amplification provides a number of important advantages. First, because measurable signals corresponding to target analytes are of higher amplitude or intensity than in the absence of amplification, exposure times and measurement times can be reduced. Second, due to the increased amplitude or intensity of measurement signals, target analytes that are present in the sample at relatively low concentrations—and whose corresponding measurement signals would otherwise be relatively weak absent amplification—can be detected with greater reliability. Third, due to the increased amplitude or intensity of measurement signals, compensation for the confounding effects of tissue autofluorescence is easier, as is the detection of the measurement signals against a background autofluorescence signal that might otherwise obscure some or all of the measurement signals.

Amplification can also be used to adjust measurement signals corresponding to different target analytes. For example, in samples where certain analytes are present at significantly smaller concentrations than other analytes, the amplitude or intensity of measurement signals corresponding to low-concentration analytes can be amplified so that they more closely match the amplitudes or intensities of signals corresponding to other target analytes in the sample that are present in higher concentrations. In this manner, the range amplitudes or intensities of the measurement signals can be reduced, so that the dynamic range of the measurement system used to detect the measurement signals can also be smaller relative to the dynamic range that would otherwise be used to measurement signals in the absence of amplification.

Further, the presence of low-concentration analytes in a sample (such as very weakly expressed biomarkers) can be visualized along with higher-concentration analytes for co-expression analysis, protein regulation assessments, and other comparative analyses that would be more challenging if both low- and higher-concentration analytes were not detected and visualized simultaneously.

When the reactive species 274 corresponds to an enzyme or other catalytic agent, the enzyme or catalytic agent can mediate the deposition of labeling agent 278 in the sample via any of a variety of different types of reactions. In some embodiments, for example (such as TSA with HRP-mediated deposition of a tyramide-conjugated labeling moiety), the reaction which is mediated by the enzyme or catalytic agent is an oxidation-reduction reaction. Other examples of suitable enzyme or catalytic agent-mediated reactions include, but are not limited to, deprotonations, eliminations, radical generation reactions, deprotections, and rearrangements.

For oxidation-reduction reactions (such as TSA with HRP-mediated deposition of labeling agent 278), a variety of different oxidation and/or reduction agents can be used. In some embodiments, for example, the oxidation agent is $H_2O_2$. A variety of other agents can also be used.

Further, it should also be noted that while in some embodiments, deposition of labeling agent 278 (or a reaction product thereof) in sample 260 is irreversible, in certain embodiments the deposition of labeling agent 278 in sample 260 is reversible, and labeling agent 278 can be removed from sample 260 following deposition by methods such as washing, one or more chemical reactions to liberate labeling agent 278, and physical methods such as heating and exposure to radiation (e.g., photocleavage or photoionization or sputtering) of the labeling agent 278.

Additional methods and aspects of TSA are described, for example, in Faget et al., *Methods Mol. Biol.* 1318: 161-172 (2015), the entire contents of which are incorporated herein by reference.

Referring again to FIGS. 5 and 6C, either before or after deposited labeling agent 278 has been detected in the sample, amplification agent 270 can optionally be removed from the sample. In particular, amplification agent 270 is hybridized to probe 200, removal of amplification agent 270 involves de-hybridizing amplification agent 270 and probe 200.

De-hybridization can also be used to control the amount of labeling agent 278 that is deposited in sample 260 (i.e., during amplification). More particularly, de-hybridization can be used to terminate the reaction (e.g., a catalytic reaction such as enzyme-mediated deposition of labeling agent 278) between reactive species 274 and labeling agent 278, thereby controlling the amount of time during which deposition of labeling agent 278 in the sample occurs.

Various methods can be used to achieve de-hybridization of probe 200 and amplification agent 270. In some embodiments, for example, de-hybridization can be achieved by exposing the sample to one or more chaotropic reagents, such as dimethyl sulfoxide (DMSO) and formamide, wherein the molar concentration of the chaotropic reagent in a solution thereof is 60% or more (e.g., 70% or more, 80% or more, 90% or more). Alternatively, de-hybridization can be performed by washing sample 260, by heating sample 260, and by combinations of the foregoing techniques.

De-hybridization followed by a washing step to remove free amplification agent 270 following de-hybridization yields a sample 260 in which probe 200 remains bound to target analyte 260, and labeling agent 278 remains deposited in sample 260 in proximity to target analyte 250. In effect, de-hybridization returns sample 260 to a state similar to that shown in FIG. 6A, with the added presence of labeling agent 278.

Some or all of the steps shown in the flow chart of FIG. 5 can optionally be repeated to selectively identify and quantify a second (and subsequent) target analyte the sample. Specifically, sample 260 can be contacted with another probe that includes a binding moiety 202 that selectively binds to a different target analyte 210 in sample 260 and a labeling species 206 that includes a different oligonucleotide. Then, the sample can be contacted with a different amplification agent that includes a reactive species (e.g., any of the reactive species described above) and an oligonucleotide that is at least partially complementary to, and hybridizes with, the oligonucleotide of the newly added probe.

Following addition of the additional amplification agent, a new labeling agent can be introduced that reacts with the reactive species to deposit the new labeling agent (or a reaction product thereof) at a location in the sample proximate to the newly added probe and amplification agent, and therefore, proximate to the second target analyte 250 to which the newly added probe selectively binds. Measured signals corresponding to the newly added labeling agent can be used to identify and quantify the second target analyte 250 in the sample.

The newly added amplification agent can again be removed from the sample via de-hybridization as described above, and additional cycles can be repetitively performed to selectively identify and quantify multiple different target analytes in the sample.

Each repetition of some or all of the steps of the flow chart in FIG. 5 is referred to as analysis cycle, and in general, any number of cycles can be performed to selectively identify and quantify different target analytes the sample. In some embodiments, for example, the number of such cycles is N, where N is 2 or more (e.g., 3 or more, 4 or more, 5 or more, 6 or more, 7 or more, 8 or more, 10 or more, 12 or more, 15 or more, or even more).

In general, for each different combination of probe and amplification agent targeting a different target analyte in the sample for analysis, a different labeling agent 278 is selectively deposited in the sample proximate to the particular target analyte. By selecting different labeling agents, different target analytes can selectively be interrogated by isolating and optionally quantifying contributions to measured emitted, reflected, or transmitted light from the sample that arise specifically from the different labeling agent. Since each labeling agent is effectively "mapped" to a different target analyte, identification and quantification of specific analytes can be achieved by isolating measurement signals corresponding to their associated labeling species.

Figure 7A:
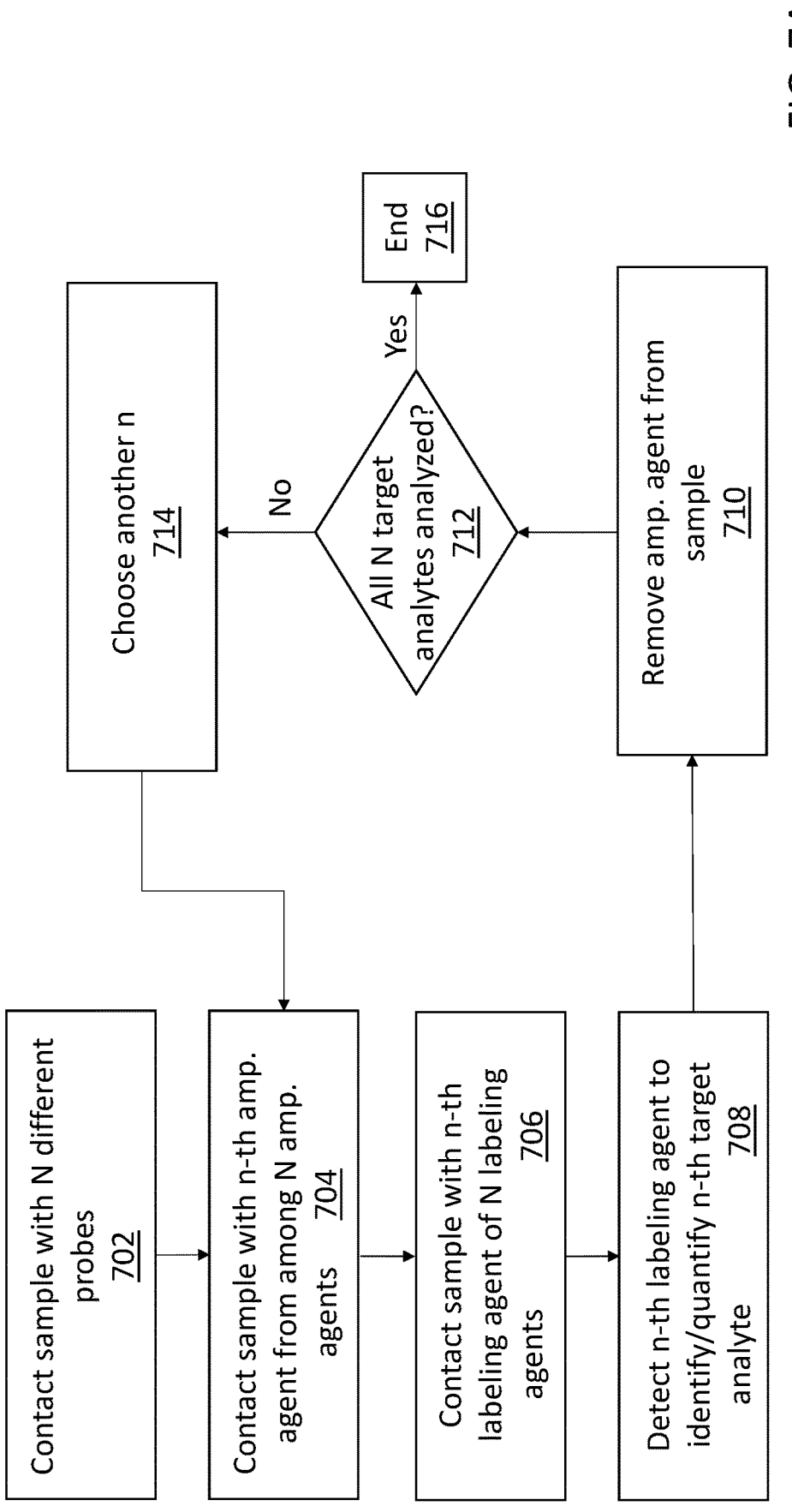
FIG. 7A is a schematic diagram showing a set of example steps for detecting multiple target analytes in a biological sample.

Multiple target analytes can also be analyzed by multiplexing the addition of different probes and amplification to the sample. FIG. 7A is a flow chart showing a series of example steps for analyzing N different target analytes in a sample. In general, N can be 2 or more (e.g., 3 or more, 4 or more, 5 or more, 6 or more, 7 or more, 8 or more, 10 or more, 12 or more, 15 or more, 20 or more, 30 or more, 40 or more, 50 or more, 60 or more, 80 or more, or even more).

In a first step 702, the sample is contacted with N different probes. Each of the N different probes includes a binding moiety 202 that specifically binds to one of the N different target analytes, and a unique oligonucleotide labeling species 206 linked to a nanobody 204 that is conjugated to the binding moiety 202. In other words, the binding moiety 202 and oligonucleotide labeling species 206 of each of the N probes are different from the binding moieties and oligonucleotide labeling species of the other probes among the N probes.

Next, in step 704, one of the n target analytes is selected for analysis, and an amplification agent that includes a reactive species conjugated to an oligonucleotide that is at least partially complementary to, and hybridizes to, the oligonucleotide labeling species 206 of the probe 200 that selectively binds the n-th target analyte is contacted to the sample. The amplification agent is thus bound to the sample at locations corresponding to the n-th target analyte (and the corresponding n-th probe).

Then, in step 706, the sample is contact with an n-th labeling agent that includes an optical moiety that is different from the optical moieties of the other (n−1) labeling agents. The labeling agent reacts with the reactive species of the n-th amplification agent, depositing the n-th labeling agent (or a reaction product thereof) in the sample in proximity to the n-th target analyte.

In step 708, the n-th labeling agent in the sample is detected, e.g., by obtaining one or more images of the sample that include optical signal contributions from the n-th labeling agent, as described previously herein. Next, in step 710, the n-th amplification agent is removed from the sample by de-hybridization and washing as described previously.

In step 712, if all N target analytes have been analyzed, the procedure terminates at step 716. If not, another n-th analyte among the N target analytes is selected for analysis, and the procedure returns to step 704.

Figure 7B:
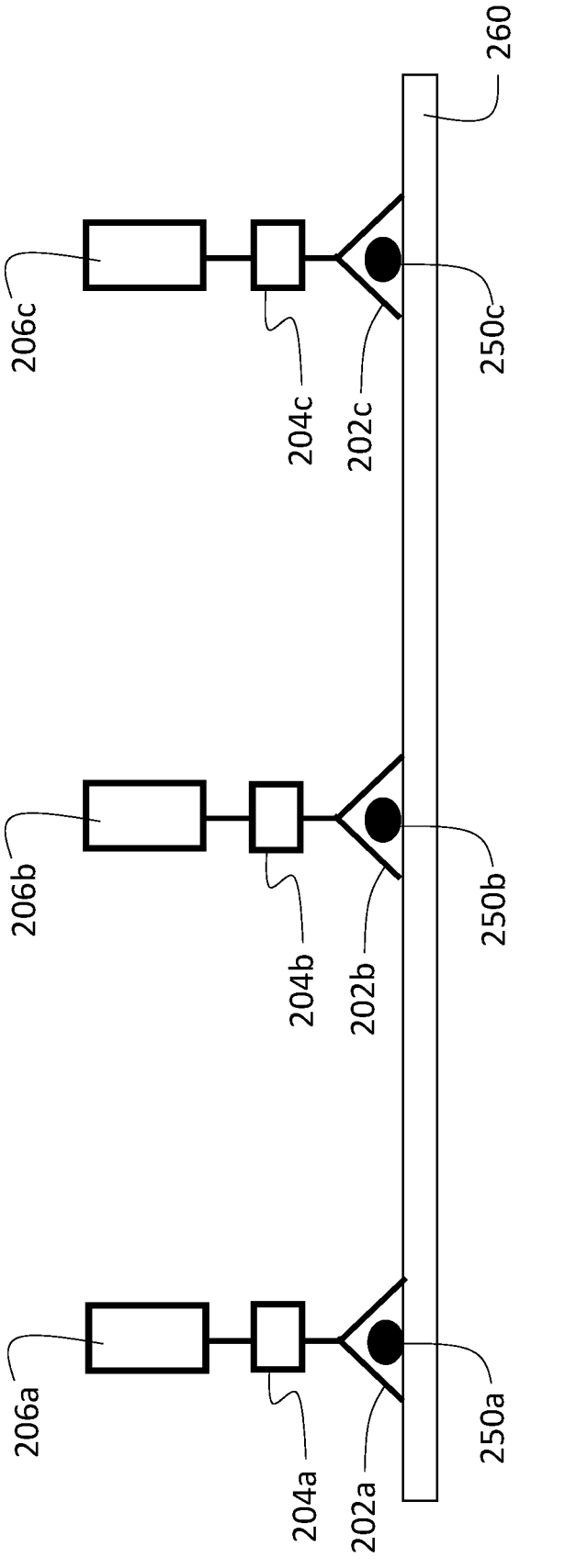
FIGS. 7B-7E are schematic diagrams showing example steps of a method for detecting multiple target analytes in a biological sample.

The foregoing procedure is illustrated schematically in FIGS. 7B-7E for a sample that includes N=3 target analytes for analysis. FIG. 7B is a schematic diagram showing a sample 260 with three different target analytes 250*a-c*. In a first step of the analysis of sample 260, three different probes are contacted to the sample, each with a different binding moiety 202*a-c* that specifically binds to a different one of the three target analytes 250*a-c*. The probes each include a different oligonucleotide labeling species 206*a*-206*c*. As shown in FIG. 7B, contacting each of the probes to the sample yields a sample in which the probes are selectively bound only to the corresponding target analytes 325*a-c* to which their binding moieties 250*a-c* are matched.

Figure 7C:
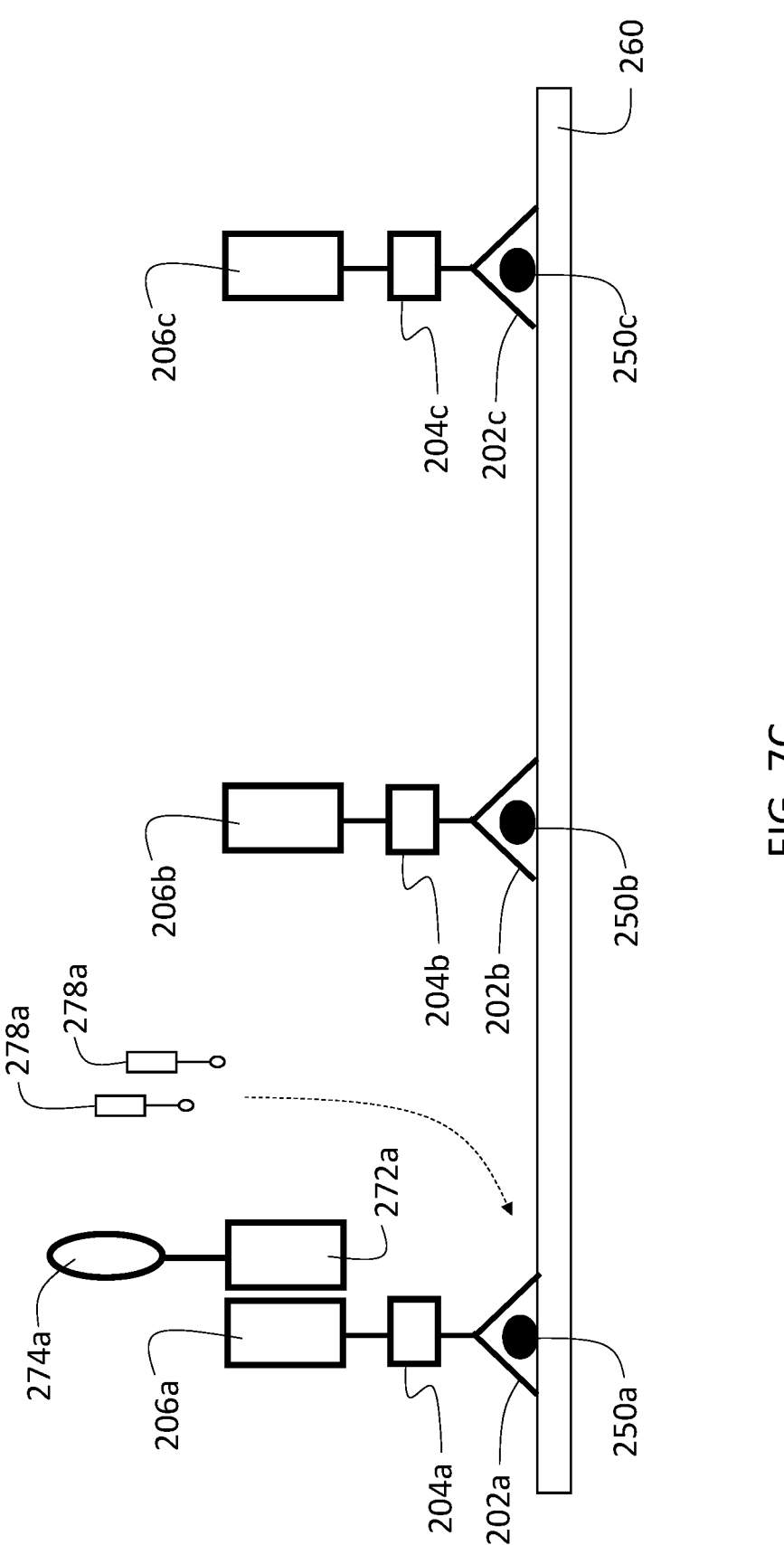
Figure 7D:
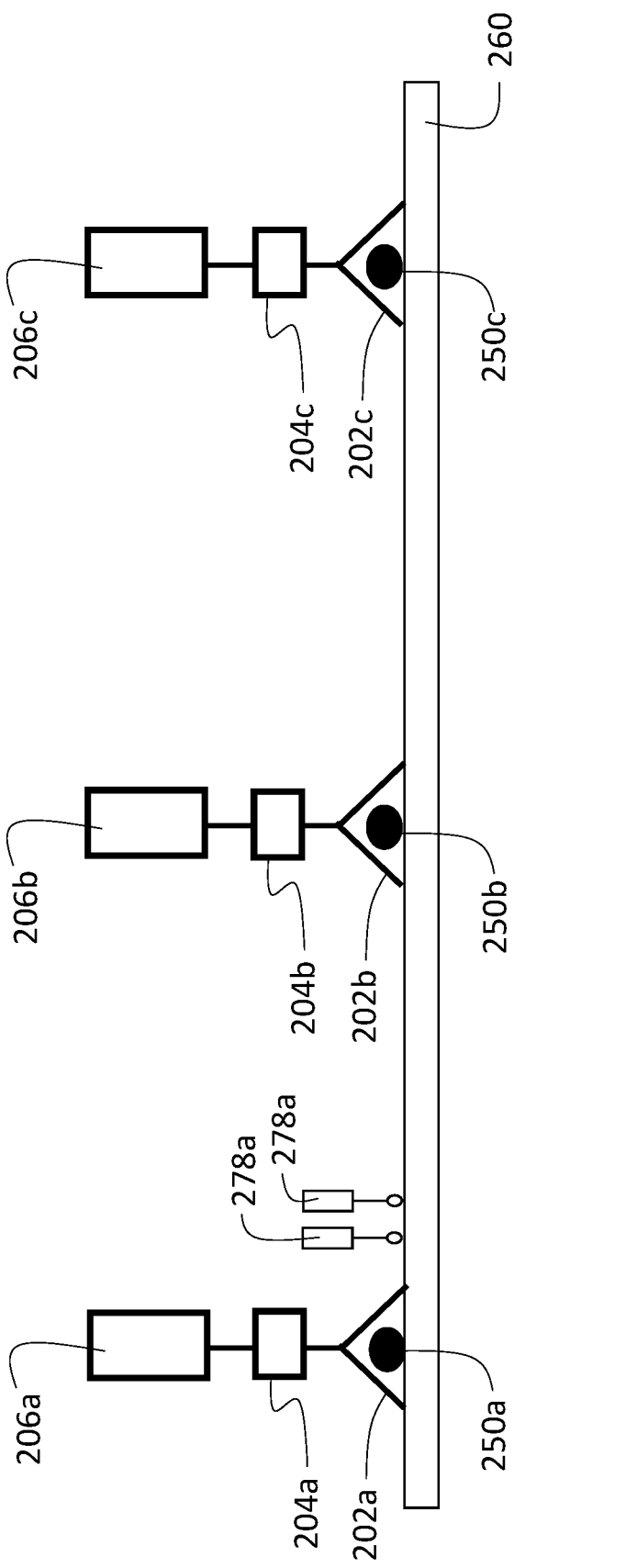
Figure 7E:
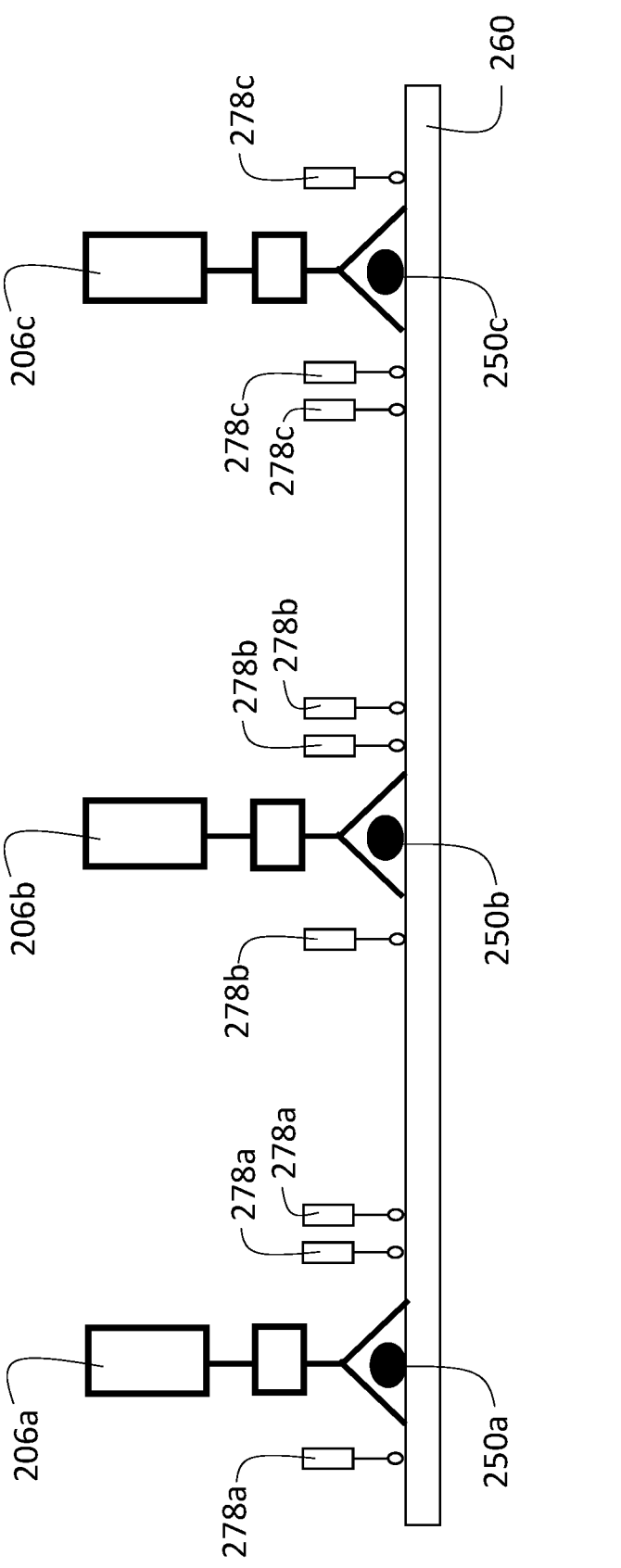

In a subsequent step of the analysis, an amplification agent that includes a reactive species 374*a* and an oligonucleotide 272*a* that is at least partially complementary to oligonucleotide labeling species 206*a* is contacted to the sample. As shown in FIG. 7C, oligonucleotide 272*a* hybridizes to oligonucleotide labeling species 206*a*, selectively binding the amplification agent to the probe bound to target analyte 250*a*. The amplification agent does not bind to either of the probes bound to target analytes 250*b* and 250*c*, owing to a lack of complementarity between oligonucleotide 272*a* and oligonucleotide labeling species 206*b* and 206*c*.

Then, as shown in FIG. 7C, a labeling agent 278*a* is contacted to the sample, and reacts with reactive agent 374*a* in the manner described above to selectively deposit labeling agent 378*a* (or a reaction product thereof) in proximity to target analyte 250*a*, as indicated by the dashed arrow.

After deposition of labeling agent 278*a*, the amplification agent is removed from sample 260 by de-hybridization and washing, as described above. The resulting sample 260 is shown schematically in FIG. 7D. Each of the different probes remains bound to corresponding different target analytes 250*a*-250*c*, and the labeling agent 278*a* remains deposited in proximity to target analyte 250*a*.

The cycle shown in FIG. 7A is repeated with amplification agents that selectively hybridize to probes bound to target analytes 250*b* and 250*c*, depositing different labeling agents 278*b* and 278*c* in proximity to target analytes 250*b* and 250*c*, respectively. After three complete cycles, sample 260 appears as shown schematically in FIG. 7E, with each of the three different probes remaining bound to their corresponding target analytes 250*a-c*, and three different labeling agents 278*a-c* deposited, respectively, in proximity to each of the three different target analytes 250*a-c*.

In general, each of the different labeling agents 278*a-c* can correspond to any of the labeling agents described above. To implement analysis of multiple target analytes in a sample, the labeling agents are generally selected such that they generate different measurement signals. For example, in embodiments where each of the labeling agents include a fluorescent or chromogenic dye moiety, the agents are selected so that each of the dye moieties have different spectral properties (e.g., absorption, emission), so that measured light emitted from, transmitted through, or reflected from the sample can separated into contributions from each of the dyes, and used to separately identify and quantify each of the target analytes 250*a-c* in the sample.

Additional aspects of the foregoing methods and further methods for using nanobody-based probes to amplify detection signals are described for example in PCT Patent Application Publication No. WO 2020/163397, the entire contents of which are incorporated herein by reference.

Samples, Target Analytes, and Reagents

The biological sample can be of animal origin, such as from a human, mouse, rat, cow, pig, sheep, monkey, rabbit, fruit fly, frog, nematode or woodchuck.

The sample can be a formalin-fixed, paraffin embedded (FFPE) tissue sample that has undergone conventional steps of de-paraffining, antigen retrieval, and blocking with bovine serum albumin (BSA). The sample can be a tissue micro-array (TMA). Alternatively, the sample can be a fresh-frozen tissue section that has undergone dehydration with graded ethanol baths prior to blocking, a fresh fixed and/or frozen tissue section, a fresh tissue section, cells obtained from a subject (e.g., via fine-needle aspirate or other technique), cultured cells, biological tissue, biological fluid, a homogenate, or an unknown biological sample.

Sample preparation can include known IHC techniques for sectioning, mounting, paraffin removal, hydration and dehydration, antigen retrieval, blocking, primary incubation, counter-staining, and other steps. These can be selected and optimized according to the goals of the assay and samples involved. Concentrations, temperatures, wash steps, and incubation times can be optimized using standard techniques such as using dilution titers and controlled experiments to assess conditions.

The sample can be immobilized on a surface. For example, the surface can be a slide, a plate, a well, a tube, a membrane, or a film. In some embodiments, the sample can be fixed using a fixative, such as an aldehyde, an alcohol, an oxidizing agent, a mercurial, a picrate, HOPE fixative, or another fixative. The sample may alternatively, or in addition, be fixed using heat fixation. Fixation can also be achieved via immersion or perfusion.

The sample can be immobilized in a three dimensional form. The three dimensional form can include, for example, a frozen block, a paraffin block, or a frozen liquid. For example, the sample can be a block of frozen animal tissue in an optimal cutting temperature compound. The block of tissue can be frozen or fixed. In some embodiments, the block of tissue can be cut to reveal a surface which can be the surface contacted by first agent as discussed above.

In some embodiments, where the sample corresponds to a block, the block can be sliced to produce serial sections of the block, each of which can be analyzed according to the methods described herein. By doing so, three dimensional information (e.g., information as a function of depth within the sample) about the identity and/or quantity of one or more target analytes in the sample can be obtained.

To detect multiple target analytes, the sample can be incubated with a composition that includes multiple detection moieties, such as multiple antibody species raised in the same animal species, of the same isotype, along with free target fragments of the materials targeted by the nanobodies of the labeling species involved in the assay, such as rabbit IgG, or mouse IgG1, IgG2a, IgG2b IgG2c or IgG3. Without wishing to be bound by theory, it is believed that this reduces the likelihood that a nanobody dissociates from an antibody of one species and finds a binding site at a different antibody species, thereby mislabeling a target analyte molecule with an improper labeling moiety 206. In this manner, migration of nanobody-based labeling moieties among different antibody species can be reduced or eliminated.

The methods described herein are suited for the identification and quantification of many different clinically relevant biomarkers in biological samples, particularly biomarkers that are expressed in tumor tissues, in the tumor microenvironment, and tissues representative of other disease states. Examples of such biomarkers that correspond to target analytes include, but are not limited to, tumor markers such as Sox10, S100, pan-cytokeratin, PAX5, PAX8; immune cell identifiers such as CD3, CD4, CD8, CD20, FoxP3, CD45RA, CD45LCA, CD68, CD163, CD11c, CD33, HLADR; activation markers such as Ki67, granzyme B; checkpoint-related markers such as TIM3, LAG3, PD1, PDL1, CTLA4, CD80, CD86, IDO-1, VISTA, CD47, CD26.

In general, the binding moiety 202 is selected to target a specific analyte in the sample. The methods described herein can be implemented with a wide variety of different types of binding moieties. For example, to target specific antigens, peptides, proteins, or other amino acid-containing species in the sample, binding moiety 202 can include an antibody (e.g., a primary antibody) or antibody fragment. The antibody or antibody fragment can include any one of different types of antibody species, including but not limited to, an immunoglobulin G (IgG), an immunoglobulin M (IgM), a polyclonal antibody, a monoclonal antibody, a single-chain fragment variable (scFv) antibody, an antigen-binding fragment (Fab), and a diabody. Antibodies and antibody fragments can be of mouse, rat, rabbit, human, camelid, or goat origin. In some embodiments, the antibody or antibody fragment can be raised against a human, mouse, rat, cow, pig, sheep, monkey, rabbit, fruit fly, frog, nematode or woodchuck antigen. In certain embodiments, the antibody or antibody fragment can be raised against an animal, plant, bacteria, fungus, or protist antigen.

In general, the various steps described herein can be implemented under a wide variety of conditions and with different reagents. Accordingly, the reagents and conditions described in this section should be understood to represent only examples of suitable reagents and conditions.

Typically, probes can be stored following preparation in a buffer solution that can include one or more of PBS, PBS-T, TBS, TBS-T, water, saline solution, and Kreb's buffer. The buffer solution can optionally include one or more blocking materials. Examples of suitable blocking materials include, but are not limited to, BSA, casein, sheared salmon-sperm DNA, oligonucleotides, rat IgG antibodies, and mouse IgG antibodies.

The amplification agents can also be stored following preparation in a buffer solution. The buffer can include one or more of PBS, PBS-T, TBS, TBS-T, water, saline solution, and Kreb's buffer. The buffer solution can be the same as, or different from, the buffer solution used to store the probes.

To promote hybridization, the sample can be contacted with a hybridization buffer. Suitable hybridization buffers can include DNA components, protein components, detergents, and/or chaotropic reagents at concentrations of between 5% and 20%.

To promote de-hybridization, the sample can be contacted with a de-hybridization buffer. Suitable hybridization buffers can include chaotropic reagents such as DMSO and/or formamide, at concentrations of between 60% and 90%.

To promote binding of a probe to a target analyte in a sample, the probe can be layered onto the sample in solution, e.g., by pipetting, and incubated with the sample. Following incubation, unbound probe can be washed from the sample using, for example, a buffer solution that includes one or more of PBS, PBS-T, TBS, TBS-T, water, saline solution, and Kreb's buffer.

The incubation time for any of the hybridization, reaction, binding, and de-hybridization steps described herein can be 10 minutes or more (e.g., 20 minutes or more, 30 minutes or more, 40 minutes or more, 60 minutes or more, 1 hour or more, 2 hours or more, 3 hours or more, 4 hours or more, 5 hours or more, 6 hours or more, 8 hours or more, 10 hours or more, 16 hours or more, 20 hours or more, 24 hours or more, 48 hours or more, 7 days or more, 30 days or more).

Reagent Kits

Also described herein are reagent kits that include any one or more of the agents, species, moieties, and reagents described herein. Such kits can include, for example, one or more of the binding moieties, one or more of the nanobody-based labeling moieties, one or more of the amplifying agents, one or more of the optical labels, and one or more of labeling agents described herein. Binding moieties and nanobody-based labeling moieties can be provided in such kits as separate entities, or in conjugated form as probes, as described herein.

Kits can include sets of different binding moieties, sets of different nanobody-based labeling moieties, sets of different probes, sets of different amplification agents, sets of different optical labels, and/or sets of different labeling agents.

Kits can be contained within a housing or packaging formed from a variety of materials including, but not limited to, plastics, glass, metals, and paper. Individual components of such kits can be contained within separate containers in a kit. Certain containers may include more than one component of a kit.

Kits can also include instructions for using any one or more of the agents, species, moieties, and reagents in the kit, and can include instructions for performing any one or more of the steps described herein. The instructions can be present in tangible form, e.g., printed on a substrate (e.g., a plastic or paper substrate), or encoded in electronic format on a storage medium such as an optical disc, a persistent storage medium such as a flash memory device, or a magnetic storage medium.

Examples

Many benefits associated with multiplexed imaging can arise from the methods described herein. In the discussion that follows, consider an assay involving multiplexed imaging of N targets in a sample. The assay is performed as a sequence of experiments, where each experiment interrogates a different set of target analytes. The overall assay (including all experiments) investigates a total of Q target analytes, which might be several hundred. In this example, the experiments use rabbit or mouse (rAb/mAb) antibodies as detection moieties.

When the assay is performed according to the methods described herein, the following advantages can be realized, relative to conventional methods for protein target analysis:

(a) The number of nanobodies that are used can be relatively low. Nanobodies can be identified, and ideally sequenced, such that nanobodies selected for use in the assay target the proper isotype for the host species used to raise the antibodies. A single nanobody targeting rabbit IgG enables using over 20,000 commercially available antibodies. Four nanobodies, targeting mouse IgG, IgG1, IgG2a kappa, and IgG2b kappa, enable using over 10,000 commercially available mouse antibodies.

(b) Nanobodies generally bind to the same site that is used in conventional secondary-antibody IHC imaging, and so binding properties of antibody-nanobody conjugates are typically well known.

(c) The nanobody binding site can be specified and is distinct from the antibody region that binds with the target compound, so antibody specificity and sensitivity are typically unaffected by the presence of the nanobody-based labeling moiety at that site on the antibody.

(d) The complexity and cost of linking a nanobody with a specific oligonucleotide labeling species is relatively low, and the labeling yield and degree is predictable because site-specific techniques can be used.

(e) The number of oligonucleotide-conjugated nanobodies is N (if only rAb are used), or a P-fold larger number (if a mix of P species and isotypes are used), but which is still of order N. In either case, this relatively small number of oligonucleotide-conjugated nanobodies enables using a vastly larger pool of antibodies, termed Q.

(f) Very flexible associations between specific oligonucleotide labeling moieties and antibodies can be achieved. Associations can be established on a per-assay basis: an antibody is incubated with a desired labeling moiety containing a nanobody linked to an oligonucleotide labeling species, and excess nanobodies are removed or inactivated in simple steps. This eliminates many of the practical problems of experimental design that arise from associating an oligonucleotide barcode with an antibody via lot-based conjugation.

(g) No requirement is established for carrier-free antibodies, which many other labeling methods require. Such antibodies can be challenging to obtain and costly.

(h) Antibody association with oligonucleotide labeling species occurs via a simple incubation so it can be performed efficiently at much smaller scale than conventional antibody conjugation, and no specialized apparatus is required.

OTHER EMBODIMENTS

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A method, comprising:
(a) contacting a biological sample with a composition comprising a plurality of different probes, wherein each different probe of the plurality of different probes comprises:
a detection moiety that selectively binds to a different protein in the sample;
a nanobody bound to the detection moiety; and
an oligonucleotide linked to the nanobody and comprising an oligonucleotide sequence, wherein the oligonucleotide sequence of each different probe of the plurality of different probes is different from the oligonucleotide sequences of each of the other different probes of the plurality of different probes;
(b) contacting the biological sample with a set of one or more different optical labels, wherein each different optical label of the set of one or more different optical labels comprises an oligonucleotide that selectively hybridizes to only one probe among the plurality of different probes, and an optical moiety; and
(c) obtaining at least one image of the biological sample, wherein the at least one image comprises optical signals generated by at least one of the optical moieties of the set of one or more different optical labels.

2. The method of claim 1, further comprising identifying one or more protein targets in the sample based on the optical signals in the at least one image of the sample.

3. The method of claim 2, further comprising determining an amount of at least one of the one or more protein targets in the sample based on the optical signals in the at least one image of the sample.

4. The method of claim 1, wherein the set of one or more different optical labels comprises multiple different optical labels.

5. The method of claim 4, wherein the set of one or more different optical labels comprises at least three different optical labels.

6. The method of claim 1, wherein the detection moiety of at least one probe of the plurality of different probes comprises an antibody or antibody fragment.

7. The method of claim 1, wherein the composition comprises at least 10 different probes.

8. The method of claim 7, wherein the composition comprises at least 30 different probes.

9. The method of claim 1, wherein the at least one of the optical moieties of the set of one or more different optical labels comprises a fluorescent dye.

10. The method of claim 1, wherein for one or more of the different probes among the plurality of different types, the nanobody is bound to the detection moiety with a dissociation constant $K_d$ that is $1.0 \times 10^{-9}$ mol/L or less.

11. The method of claim 1, wherein the composition comprises multiple different probes comprising antibody binding moieties of a common species and isotype.

12. The method of claim 1, wherein the composition further comprises at least one fragment of a binding target of at least one of the nanobodies among the plurality of different probes.

13. The method of claim 12, wherein the composition further comprises multiple different fragments of binding targets of multiple nanobodies among the plurality of different probes.

14. The method of claim 1, further comprising, prior to contacting the sample with the composition, forming each of the different probes of the plurality of different probes, wherein each different probe of the plurality of different probes is formed by:
contacting the detection moiety for the different probe of the plurality of different probes with a labeling moiety comprising the nanobody for the different probe of the plurality of different probes linked to the oligonucleotide for the different probe of the plurality of different probes; and
incubating the binding moiety and the labeling moiety to bind the nanobody to the binding moiety.

15. The method of claim 14, wherein the nanobody undergoes site-specific binding to the binding moiety.

16. The method of claim 1, further comprising, following step (a), contacting the sample with at least one fixative.

17. The method of claim 1, further comprising, following step (a), washing the sample to remove unbound probes from the sample.

18. The method of claim 1, wherein at least one optical label of the set of one or more different optical labels comprises the oligonucleotide of the at least one optical label of the set of one or more different optical labels linked to the optical moiety of the at least one optical label of the set of one or more different optical labels through a strepta-vidin-biotin linkage.

19. The method of claim 1, wherein the at least one image comprises at least one fluorescence image of the sample.

20. The method of claim 1, further comprising repeating steps (b)-(c) with at least one additional set of one or more different optical labels, to obtain at least one additional image of the sample comprising optical signals generated by at least one of the optical moieties of the at least one additional set of one or more different optical labels.

21. The method of claim 20, further comprising identi-fying one or more additional protein targets in the sample based on the optical signals in the at least one additional image of the sample.

22. The method of claim 20, further comprising, for each sequence of steps (b)-(c), removing the set of one or more different optical labels from the sample prior to repeating step (b) with at least one additional set of one or more different optical labels.

23. The method of claim 22, wherein removing the set of one or more different optical labels comprises dehybridizing the set of one or more different optical labels from the plurality of different probes.

* * * * *